(12) United States Patent
Glezer et al.

(10) Patent No.: US 11,065,615 B2
(45) Date of Patent: Jul. 20, 2021

(54) ASSAY MODULES HAVING ASSAY REAGENTS AND METHODS OF MAKING AND USING SAME

(71) Applicant: MESO SCALE TECHNOLOGIES, LLC, Rockville, MD (US)

(72) Inventors: Eli N. Glezer, Chevy Chase, MD (US); Bandele Jeffrey-Coker, Darnestown, MD (US); Jeffery D. Debad, Gaithersburg, MD (US); Sudeep M. Kumar, Gaithersburg, MD (US); George B. Sigal, Rockville, MD (US); Gisbert Spieles, Bethesda, MD (US); Michael Tsionsky, Derwood, MD (US); Michael Warnock, Carlsbad, CA (US)

(73) Assignee: MESO SCALE TECHNOLOGIES, LLC, Rockville, MD (US)

( * ) Notice: Subject to any disclaimer, the term of this patent is extended or adjusted under 35 U.S.C. 154(b) by 697 days.

(21) Appl. No.: 15/882,914

(22) Filed: Jan. 29, 2018

(65) Prior Publication Data

US 2018/0154353 A1    Jun. 7, 2018

Related U.S. Application Data

(60) Continuation of application No. 13/662,553, filed on Oct. 29, 2012, now Pat. No. 9,878,323, which is a
(Continued)

(51) Int. Cl.
*G01N 33/543* (2006.01)
*B01L 3/00* (2006.01)
*G01N 33/53* (2006.01)

(52) U.S. Cl.
CPC ........... *B01L 3/5025* (2013.01); *B01L 3/5085* (2013.01); *G01N 33/5304* (2013.01);
(Continued)

(58) Field of Classification Search
CPC .. B01L 3/5025; B01L 3/5085; B01L 2200/12; B01L 2200/16; B01L 2300/0636;
(Continued)

(56) References Cited

U.S. PATENT DOCUMENTS

| 4,450,231 A | 5/1984 | Ozkan |
| 4,735,778 A | 4/1988 | Maruyama et al. |

(Continued)

FOREIGN PATENT DOCUMENTS

| CN | 1549921 | 11/2004 |
| EP | 0321260 | 6/1989 |

(Continued)

OTHER PUBLICATIONS

Int'l Search Report for PCT/US2006/049048, four pages (Dec. 2007).
(Continued)

*Primary Examiner* — Christopher L Chin
(74) *Attorney, Agent, or Firm* — Nixon & Vanderhye, PC

(57) ABSTRACT

We describe assay modules (e.g., assay plates, cartridges, multi-well assay plates, reaction vessels, etc.), processes for their preparation, and method of their use for conducting assays. Reagents may be present in free form or supported on solid phases including the surfaces of compartments (e.g., chambers, channels, flow cells, wells, etc.) in the assay modules or the surface of colloids, beads, or other particulate supports. In particular, dry reagents can be incorporated into the compartments of these assay modules and reconstituted prior to their use in accordance with the assay methods. A desiccant material may be used to maintain and stabilize these reagents in a dry state.

14 Claims, 8 Drawing Sheets

Related U.S. Application Data continuation of application No. 12/871,946, filed on Aug. 31, 2010, now Pat. No. 8,298,834, which is a division of application No. 11/642,970, filed on Dec. 21, 2006, now Pat. No. 7,807,448.

(60) Provisional application No. 60/752,745, filed on Dec. 21, 2005, provisional application No. 60/752,513, filed on Dec. 21, 2005.

(52) U.S. Cl.
CPC . *G01N 33/54366* (2013.01); *G01N 33/54393* (2013.01); *B01L 2200/12* (2013.01); *B01L 2200/16* (2013.01); *B01L 2300/0636* (2013.01); *B01L 2300/0645* (2013.01); *B01L 2300/0829* (2013.01); *B01L 2300/0851* (2013.01); *B01L 2300/0858* (2013.01); *B01L 2300/105* (2013.01); *Y10S 436/809* (2013.01)

(58) Field of Classification Search
CPC ..... B01L 2300/0645; B01L 2300/0829; B01L 2300/0851; B01L 2300/0858; B01L 2300/105; B01L 9/523; G01N 33/54366; G01N 33/54393; G01N 33/5304; G01N 35/028; Y10S 436/809; B01J 2219/00315; B01J 2219/00317
USPC ....... 422/407, 552, 553; 436/809; 435/288.4
See application file for complete search history.

(56) References Cited

U.S. PATENT DOCUMENTS

| | | | |
|---|---|---|---|
| 4,770,856 A | | 9/1988 | Uthemann et al. |
| 4,828,386 A | | 5/1989 | Matkovich et al. |
| 4,895,706 A | * | 1/1990 | Root ........................ B01D 61/18 422/534 |
| 4,988,618 A | | 1/1991 | Li et al. |
| 4,988,627 A | | 1/1991 | Smith-Lewis |
| 5,084,246 A | * | 1/1992 | Lyman ................ B01L 3/50255 356/246 |
| 5,110,556 A | * | 5/1992 | Lyman ................ B01L 3/50255 356/246 |
| 5,312,744 A | | 5/1994 | Shibata |
| 5,378,638 A | | 1/1995 | Deeg et al. |
| 5,766,554 A | | 6/1998 | Liu |
| 6,096,562 A | | 8/2000 | Bunn et al. |
| 6,296,020 B1 | | 10/2001 | McNeely et al. |
| 6,429,026 B1 | | 8/2002 | Pettersson et al. |
| 6,483,585 B1 | | 11/2002 | Yang |
| 6,591,852 B1 | | 7/2003 | McNeely et al. |
| 6,601,613 B2 | | 8/2003 | McNeely et al. |
| 6,635,430 B1 | | 10/2003 | Tortorella |
| 6,977,722 B2 | | 12/2005 | Wohlstadter et al. |
| 7,063,946 B2 | | 6/2006 | Kenten et al. |
| 7,198,759 B2 | | 4/2007 | Bryning et al. |
| 7,384,779 B2 | | 6/2008 | Fang et al. |
| 7,497,997 B2 | | 3/2009 | Glezer et al. |
| 7,618,829 B2 | | 11/2009 | Keizer et al. |
| 7,807,448 B2 | | 10/2010 | Glezer et al. |
| 7,842,246 B2 | | 11/2010 | Wohlstadter et al. |
| 7,858,321 B2 | | 12/2010 | Glezer et al. |
| 8,012,745 B2 | | 9/2011 | Glezer et al. |
| 8,298,834 B2 | | 10/2012 | Glezer et al. |
| 9,878,323 B2 | | 1/2018 | Glezer et al. |
| 2002/0036018 A1 | | 3/2002 | McNeely et al. |
| 2003/0059766 A1 | | 3/2003 | Goertz et al. |
| 2003/0207290 A1 | | 11/2003 | Kenten et al. |
| 2004/0022677 A1 | | 2/2004 | Wohlstadter et al. |
| 2004/0109793 A1 | | 6/2004 | McNeely et al. |
| 2004/0171087 A1 | * | 9/2004 | Rech-Weichselbraun .................. G01N 33/54393 435/7.5 |
| 2004/0189311 A1 | | 9/2004 | Glezer et al. |
| 2005/0052646 A1 | | 3/2005 | Wohlstadter et al. |
| 2005/0142033 A1 | | 6/2005 | Glezer et al. |
| 2007/0041878 A1 | | 2/2007 | Bryning et al. |
| 2007/0258415 A1 | | 5/2007 | Bryning et al. |
| 2007/0202538 A1 | | 8/2007 | Glezer et al. |
| 2007/0231217 A1 | | 10/2007 | Glezer et al. |
| 2007/0269839 A1 | | 11/2007 | Goertz et al. |
| 2008/0044928 A1 | | 2/2008 | Char et al. |
| 2009/0258415 A1 | | 10/2009 | Bryning et al. |
| 2011/0059870 A1 | | 3/2011 | Wohlstadter et al. |
| 2011/0203924 A1 | | 8/2011 | Wohlstadter et al. |
| 2012/0190590 A1 | | 7/2012 | Wohlstadter et al. |
| 2012/0190591 A1 | | 7/2012 | Wohlstadter et al. |

FOREIGN PATENT DOCUMENTS

| | | |
|---|---|---|
| EP | 0947831 | 10/1999 |
| JP | 2002-535620 | 10/2002 |
| JP | 2003-506697 | 2/2003 |
| JP | 2004-534226 | 11/2004 |
| JP | 2005-513441 | 5/2005 |
| JP | 2005-521032 | 7/2005 |
| JP | 2005-534044 | 11/2005 |
| WO | 00/42432 | 7/2000 |
| WO | 01/28683 | 4/2001 |
| WO | 03/023360 | 3/2003 |
| WO | 03/052428 | 6/2003 |
| WO | 2004/011147 | 2/2004 |
| WO | 2004/061418 | 7/2004 |
| WO | 2005/062050 | 7/2005 |

OTHER PUBLICATIONS

Written Opinion of ISA for PCT/US2006/049048, six pages (Dec. 2007).
Int'l Preliminary Report on Patentability for PCT/US2006/049048, seven pages (Jun. 2008).
Supplementary European search report and search opinion for EP 15193494.0, five pages (May 2016).
Supplementary European search report and search opinion for EP 06846006.2, ten pages, (Apr. 2014).
First Office Action and search report in CN 201210109497.1, six pages (Mar. 2014). In lieu of an English translation of the CN patent application cited therein, the SIPO's concise explanations of relevance and what are believed to be US counterparts are provided.
Notification of Reason for Rejection in JP 2008-547612, five pages (Feb. 2012). In lieu of English translations of the three Japanese patent documents cited therein, the JPO's concise explanations of relevance and what are believed to be US counterparts were provided.
Notification of Reasons for Rejection in JP 2012-179913, three pages (Jan. 2014). In lieu of English translations of the three Japanese patent documents cited therein, the JPO's concise explanations of relevance and what are believed to be US counterparts were provided.
Thorpe et al. "A stable lyophilized reagent for use in a potential reference assay for quantitation of anti-D in immunoglobulin products" *Biologicals*, vol. 30, No. 4, pp. 315-321 (Dec. 2002).
Qin et al. "Time-resolved fluorescence resonance energy transfer assay for point-of-care testing of urinary albumin" *Clinical Chemistry*, vol. 49, No. 7, pp. 1105-1113 (Jul. 2003).

\* cited by examiner

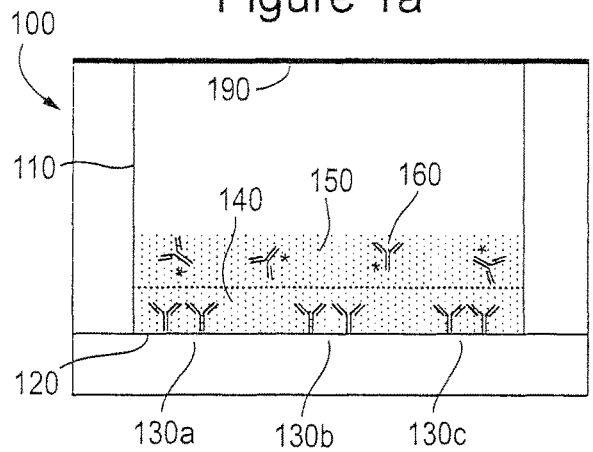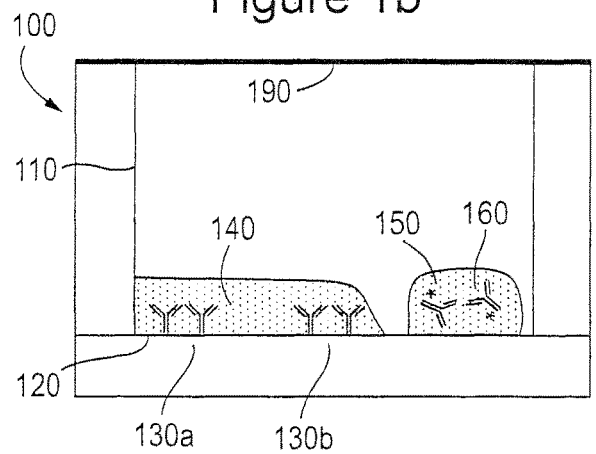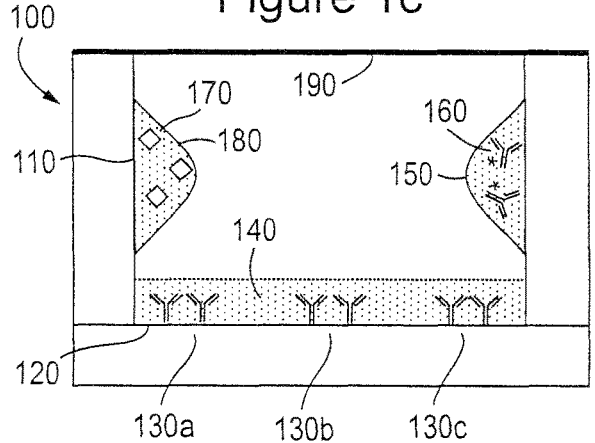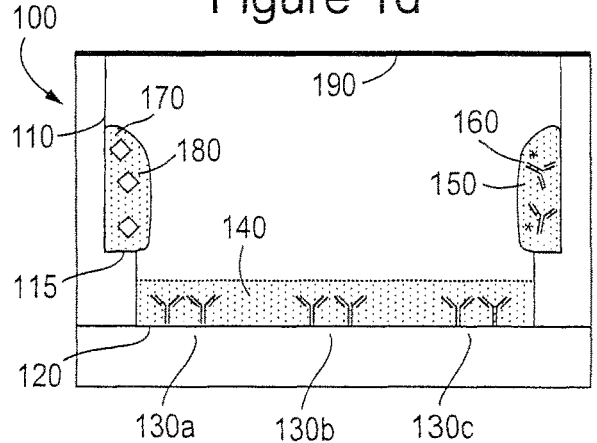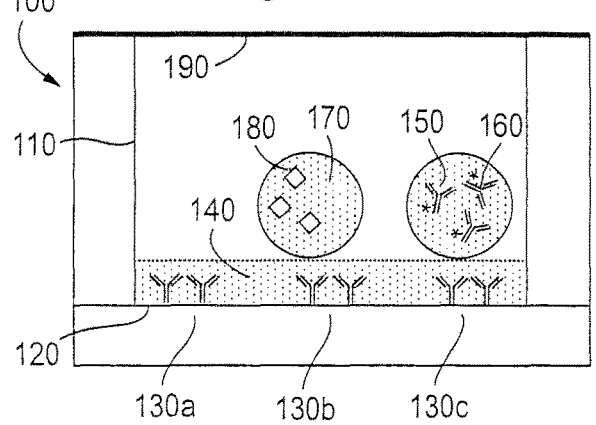

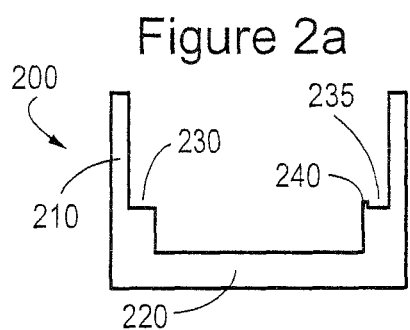
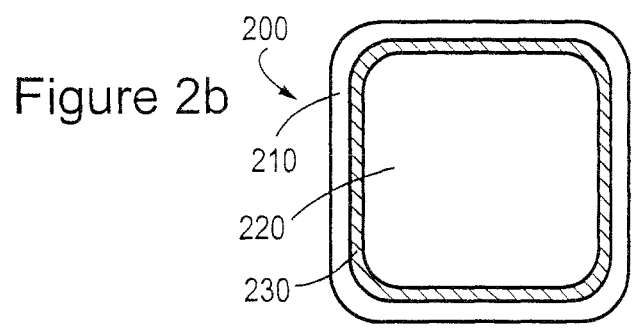
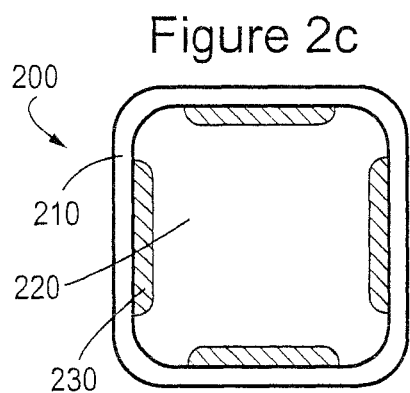
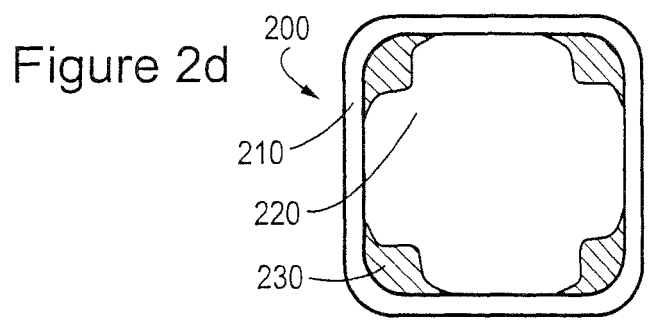
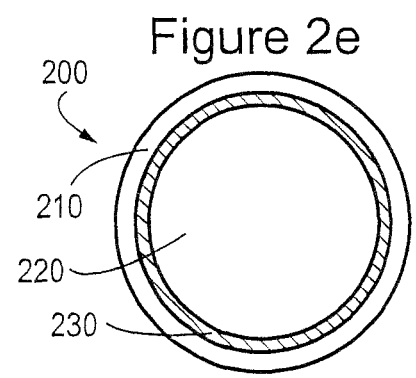
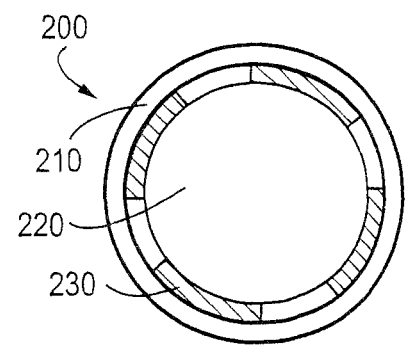
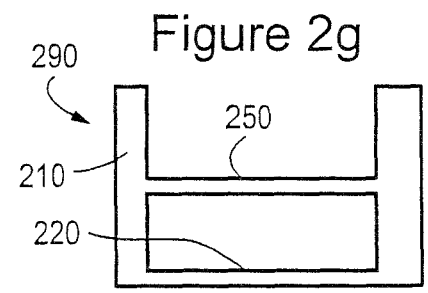
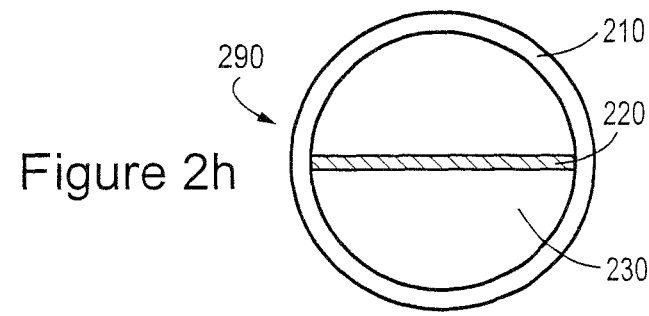
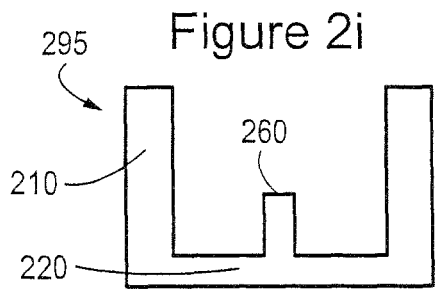
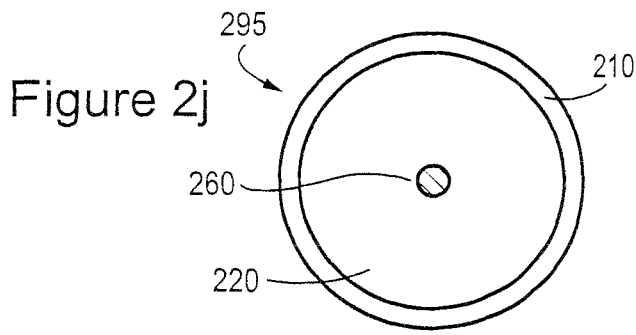

ASSAY MODULES HAVING ASSAY REAGENTS AND METHODS OF MAKING AND USING SAME

CROSS-REFERENCE TO RELATED APPLICATIONS

This application is a continuation of application Ser. No. 13/662,553, filed Oct. 29, 2012, now allowed; which is a continuation of application Ser. No. 12/871,946, filed Aug. 31, 2010, now U.S. Pat. No. 8,298,834; which is a division of application Ser. No. 11/642,970, filed Dec. 21, 2006, now U.S. Pat. No. 7,807,448; which claims benefit of Provisional Application No. 60/752,475, filed Dec. 21, 2005, and benefit of Provisional Application No. 60/752,513, filed Dec. 21, 2005; each of which is hereby incorporated by reference.

STATEMENT REGARDING FEDERALLY-SPONSORED RESEARCH

This invention was made with federal support under HDTRA1-05-C-0005 awarded by Department of Defense. The U.S. government has certain rights in the invention.

FIELD OF THE INVENTION

The invention relates to assay modules, such as assay plates, cartridges, multi-well assay plates, reaction vessels, and methods for conducting chemical, biochemical, and/or biological assays. The invention also relates to the incorporation of dry reagents into these modules and/or the use dry reagent in these methods.

BACKGROUND OF THE INVENTION

Numerous methods and systems have been developed for conducting chemical, biochemical, and/or biological assays. These methods and systems are essential in a variety of applications including medical diagnostics, food and beverage testing, environmental monitoring, manufacturing quality control, drug discovery, and basic scientific research.

Depending on the application, it is desirable that assay methods and systems have one or more of the following characteristics: i) high throughput, ii) high sensitivity, iii) large dynamic range, iv) high precision and/or accuracy, v) low cost, vi) low consumption of reagents, vii) compatibility with existing instrumentation for sample handling and processing, viii) short time to result, ix) multiplexing capability, and x) insensitivity to interferents and complex sample matrices. It is also desirable in many applications that these types of performance benefits are achieved with assay formats that are easy to carry out, are amenable to automation, and/or use stable dry reagents. There is substantial value to new assay methods and systems with these characteristics.

A variety of approaches have been developed that provide reagents for assays in dry stable form. U.S. Pat. No. 5,413,732 describes certain dry reagent spheres that are capable of dissolving in a solution.

U.S. Pat. No. 6,429,026 describes certain immunoassays using dry reagents and time-resolved fluorescence detection. A catching antibody is immobilized on the surface of a microtitration well. An insulating layer containing carbohydrate and/or protein is dried on top of the catching antibody at the bottom of the well. A labeled antibody is added in a small volume and dried on top of the insulating layer. The antibody is labeled with a lanthanide chelate that can be detected using dissociation enhance lanthanide fluoroimmunoassay (DELFIA) techniques. To start the immunoassay, a sample and a common assay buffer is added. After allowing the antibody reactions to occur, the well is washed several times, a DELFIA enhancement buffer is added, and a fluorescence lifetime measurement is carried out.

U.S. Publication 2003/0108973 describes a sandwich immunoassay that employed a test tube containing a lyophilized mixture comprising a capture antibody immobilized on 2.8 µm magnetizable polystyrene beads and a detection antibody labeled with an electrochemiluminescent label. The mixture could also include blocking agents to reduce non-specific binding of the detection antibody to the beads during the lyophilization process. Addition of sample containing the analyte of interest resulted in the formation of sandwich complexes on the beads. A suspension of beads was then aspirated into a reusable flow cell where they were collected on an electrode and analyzed using electrochemiluminescence (ECL) detection techniques.

U.S. Pat. No. 6,673,533 of Wohlstadter et al. describes an ECL-based sandwich immunoassay using dry reagents. A capture antibody was immobilized on a composite electrode. The other reagents used in assay were dried on the electrode surface by adding and lyophilizing a solution containing a detection antibody linked to an ECL label, phosphate, tripropylamine, bovine serum albumin, sucrose, chloracetamide, and TRITON X-100. Immunoassays were conducted by adding a sample to the dried reagents on the electrodes, incubating the solutions, and applying a potential to the electrode to induce ECL. No washing step was required.

A variety of techniques have been developed for increasing assay throughput. The use of multi-well assay plates (also known as microtiter plates or microplates) allows for the parallel processing and analysis of multiple samples distributed in multiple wells of a plate. Multi-well assay plates can take a variety of forms, sizes, and shapes. For convenience, some standards have appeared for instrumentation used to process samples for high-throughput assays. Multi-well assay plates typically are made in standard sizes and shapes, and have standard arrangements of wells. Arrangements of wells include those found in 96-well plates (12×8 array of wells), 384-well plates (24×16 array of wells), and 1536-well plates (48×32 array of wells). The Society for Biomolecular Screening has published recommended microplate specifications for a variety of plate formats (see http://www.sbsonline.org).

U.S. Publications 2004/0022677 and 2005/0052646 of U.S. application Ser. Nos. 10/185,274 and 10/185,363, respectively, of Wohlstadter et al. describe solutions that are useful for carrying out singleplex and multiplex ECL assays in a multi-well plate format. They include plates that comprise a plate top with through-holes that form the walls of the wells and a plate bottom sealed against the plate top to form the bottom of the wells. The plate bottom has patterned conductive layers that provide the wells with electrode surfaces that act as both solid-phase supports for binding reactions as well as electrodes for inducing ECL. The conductive layers may also include electrical contacts for applying electrical energy to the electrode surfaces.

Despite such known methods and systems for conducting assays, improved assay modules for conducting chemical, biochemical, and/or biological assays are needed.

SUMMARY OF THE INVENTION

The invention relates to assay modules (e.g., assay plates, cartridges, or multi-well assay plates, reaction vessels, etc.), having assay reagents pre-loaded in the wells, chambers or assay regions of the assay module. In certain embodiments, these assay reagents are stored in a dry state. Furthermore, the assay modules may comprise desiccant materials for maintaining these assay reagents in a stable dry state. A method is provided for making such assay modules and methods for using the assay modules in assays.

A multi-well plate is provided comprising at least one well having (1) a binding surface having a first binding reagent immobilized thereon and (2) at least one additional dry reagent, wherein at least one additional dry reagent does not contact the binding surface. The multi-well plate may have an electrode surface with a binding surface incorporated in at least one well of the multi-well plate.

A multi-well assay plate is provided comprising a plate body with a plurality of wells defined therein, the plurality of wells comprising a binding surface having a capture reagent immobilized thereon and a reconstitutable dry reagent. Optionally, the binding surface may be selected to be suitable for use as an electrode in an electrochemical assay or electrochemiluminescence assay. Furthermore, the binding surfaces may be coated with a reconstitutable protective layer. The dry reagent, which may be a labeled detection reagent, is free standing or located on a surface of the well that does not overlap with the binding surface. In one specific example, the binding surface is located on the bottom of the well and the reconstitutable dry reagent is located on a wall of the well and, optionally, on a reagent storage shelf defined on the wall. In another example, the binding surface and the reconstitutable dry reagent are both located on non-overlapping regions of the bottom surface of the well. In another specific example, the reconstitutable dry reagent is a free-standing pill.

The multi-well assay plate may further comprise a reconstitutable dry assay control analyte which may have binding affinity for the immobilized capture reagent and/or, if present, the labeled detection reagent. In certain embodiments, the control analyte has affinity for immobilized capture reagents and/or labeled detection reagents within the well, but is present in unbound form that is not in contact with the binding surface or labeled detection reagent.

The multi-well assay plate may further comprise one or more additional immobilized capture reagents. The capture reagent and additional capture reagents are patterned on the binding surface to form an array of binding domains on the binding surface. These binding domains/capture reagents may differ in specificity or affinity for binding partners. In addition, the wells may contain a plurality of different reconstitutable dry labeled detection reagents that differ in specificity or affinity for binding partners.

The multi-well plates, described above, may be used in methods of carrying out assays comprising adding sample to one or more of the wells of a plate comprising immobilized capture reagents and reconstitutable dry labeled detection reagents, reconstituting reconstitutable dry materials in these wells to form a reaction mixture(s), incubating the reaction mixture(s) under conditions that promote binding of said capture and detection reagents to their corresponding binding partners, and measuring the formation of complexes comprising the immobilized capture reagents and labeled binding reagents. By appropriate choice of capture and detection reagents, these methods may include sandwich binding assay methods and competitive binding assay methods.

A method is provided of preparing multi-well assay plates for use in an assay comprising carrying out the following on at least two wells of a plate: immobilizing a capture reagent on a surface of a well of said plate to form a binding surface, dispensing a liquid reagent comprising a labeled detection reagent to a surface of the well that does not overlap the binding surface, and drying the liquid reagent to form a reconstitutable dry detection reagent. The method may also include, dispensing a protecting reagent on the binding surface and drying the protecting reagent to form a reconstitutable dry protective layer on the binding surface. For example, the protecting reagent is dispensed and dried prior to dispensing the liquid reagent comprising a labeled detection reagent.

In certain specific embodiments, the binding surface is on a bottom surface of the well and the liquid reagent is dispensed and dried on a non-overlapping bottom surface of the well or on a wall of the well. Optionally, the wall comprises a liquid storage shelf and the liquid reagent is (i) dispensed and dried on the shelf or (ii) dispensed on the wall at a location above the shelf such that liquid reagent that runs down the wall collects and is subsequently dried on the shelf.

The methods for preparing plates may further comprise immobilizing one or more additional capture reagents so as to form an array of binding domains on the binding surface that differ in their specificity or affinity for binding partners. Similarly, the liquid reagent may comprise one or more additional labeled detection reagents that differ in their specificity or affinity for binding partners. Furthermore, the method may include dispensing and drying an additional liquid reagent comprising an assay control analyte with binding affinity for the capture or labeled detection reagent, the additional liquid reagent being dispensed and dried such that it does not contact the capture or labeled detection reagents.

In certain alternate embodiments of the methods described above, dispensing and drying a liquid reagent comprising a labeled detection reagent are omitted and a reconstitutable dry labeled detection reagent is added in free-standing form, for example, as a free-standing pill. Preferably, prior to adding the detection reagent, a protecting reagent is dispensed and dried on the binding surface to form a reconstitutable protective layer. The method may also include immobilizing one or more additional capture reagents so as to form an array of binding domains on said binding surface that differ in their specificity or affinity for binding partners. Similarly, the reconstitutable dry reagent may comprise one or more additional labeled detection reagents that differ in their specificity or affinity for binding partners. Furthermore, the method may include adding to the well an additional free standing dry reagent comprising an assay control analyte that has binding affinity for the capture and/or detection reagents.

A multi-well plate is provided comprising a plate body with a plurality of wells defined therein including: a) a plurality of first reagent wells holding a reconstitutable first dry reagent and b) a plurality of second reagent wells holding a second dry reagent, wherein, the first and second reagents are matched reagents for conducting an assay. A method is provided for carrying out assays in these plates comprising: a) adding a sample to one of the first reagent wells, b) reconstituting reconstitutable dry labeled detection reagents in the first reagent well to faint a reaction mixture, c) transferring an aliquot of the reaction mixture to one or more of the second reagent wells, and d) incubating the reaction mixture in the second reagent well(s) so as to carry out said assay on said sample. In one embodiment, the multi-well assay plate can be divided into a plurality of sets of wells consisting of one first reagent well and one or more second reagent wells and the method further comprises repeating the process of (a)-(d) for each set of wells.

In one specific embodiment of the multi-well plate having first and second reagent wells, the first reagent wells are arranged in a regular two dimensional pattern and said first reagent wells have well floors and well walls, the well walls having inner wall surfaces and outer wall surfaces. Furthermore, the second reagent wells have well floors and well walls, the well walls being defined by outer wall surfaces of the detection wells and by rib elements connecting the outer wall surfaces of adjacent detection wells. Optionally, the first reagent wells have well opening perimeters that are round and/or the first reagent wells are arranged in an 8×12 square array.

A multi-well assay plate is provided comprising a plate body with a plurality of wells defined therein including: a) a plurality of detection wells, each detection well comprising a binding surface having a capture reagent immobilized thereon and b) a plurality of reagent reconstitution wells, each reagent reconstitution well comprising a reconstitutable labeled detection reagent, wherein, at least one detection well and one reagent reconstitution well comprise matched capture and detection reagents for measuring an analyte of interest. Optionally, the binding surface may be selected to be suitable for use as an electrode in an electrochemical or electrochemiluminescence assay. In one embodiment, the detection and reagent reconstitution wells are grouped into a plurality of assay sets consisting of one reagent reconstitution well and one or more detection wells, the reagent reconstitution well and detection wells within a set comprising matched capture and detection reagents for measuring an analyte of interest. These sets may consist of one reagent reconstitution well and one detection well.

One specific embodiment of the multi-well plate with a detection wells and reagent reconstitution wells includes:
a) a plurality of detection wells, wherein said detection wells,
 i) have well floors and well walls, said well walls having inner wall surfaces and outer wall surfaces,
 ii) are arranged in a regular two dimensional pattern, and
 iii) comprise, on an inner surfaces of each of said detection wells, a binding surface having a capture reagent immobilized thereon array;
b) a plurality of reagent reconstitution wells, wherein said reagent reconstitution wells
 i) have a well floors and well walls, said well walls being defined by outer wall surfaces of said detection wells and by rib elements connecting the outer wall surfaces of adjacent detection wells, and
 ii) comprise, in each reagent reconstitution well, a reconstitutable dry labeled detection reagent.

Optionally, the detection wells have well opening perimeters that have no reentrant angles or curves (e.g., round perimeters) and the reagent reconstitution wells have well opening perimeters with reentrant angles or curves.

The detection or reagent reconstitution wells of the multi-well plates with detection wells and reagent reconstitution wells may further comprise a reconstitutable dry assay control analyte. The detection wells may also comprise one or more additional immobilized capture reagents. In this embodiment, the capture reagents are patterned to foul' a patterned array of binding domains on the binding surface that differ in specificity or affinity for binding partners. Furthermore, the reconstitutable dry reagent may further comprise one or more additional labeled detection reagents, the detection reagent and additional detection reagents differing in specificity or affinity for binding partners.

A method is provided for carrying out assays in multi-well plates with detection wells and reagent reconstitution wells. One embodiment comprises a) adding a sample to one of the reagent reconstitution wells, b) reconstituting reconstitutable dry labeled detection reagents in the reconstitution well to form a reaction mixture(s), c) transferring an aliquot of the reaction mixture to one or more detection wells, c) incubating the reaction mixture in the detection well(s) under conditions that promote binding of the capture and detection reagents to their corresponding binding partners, and d) measuring the formation of complexes comprising the immobilized capture reagents and the labeled binding reagent. Optionally, the multi-well assay plate can be divided into a plurality of sets of wells consisting of one first reagent well and one or more second reagent wells and the method further comprises repeating the process of (a)-(d) for each of said set of wells.

A multi-well assay plate is provided comprising a plate body with a plurality of wells defined therein having well floors and well walls that extend from said floors to a height $h_w$ above said floors, said walls being shaped so as to provide shelf elements at a height $h_s$, wherein $0<h_s<h_w$. The wells may be arranged in standard multi-well plate formats including 4×6, 8×12, 16×24, and 32×48 arrays of wells arranged in square lattices. In certain embodiments, $h_s$ is greater than or equal to 0.02 $h_w$, 0.05 $h_w$, or 0.1 $h_w$ but less than or equal to 0.1 $h_w$, 0.25 $h_w$ or 0.5 $h_w$. In other embodiments, $h_s$ is greater or equal to about 0.1 mm, 0.2 mm 0.5 mm, or 1 mm but less than or equal to about 1 mm, 2 mm, or 5 mm. The shelf elements may be used to hold dry reagents. Thus, another embodiment is a plate with reconstitutable dry reagents on the shelves. A method is provided for preparing plates for use in an assay that comprise dispensing a liquid reagent in a well of a multi-well plate that has a shelf element and drying the reagent to form a reconstitutable dry reagent, wherein the reagent is dispensed and dried on the shelf or dispensed on the wall above the shelf and dried such that liquid reagent that runs down the well wall collects on and is dried on the shelf.

In certain embodiments of the plate with wells with shelf elements, the plate body is a one-piece injection-molded part. In other embodiments, the plate body comprises a plate top having a plurality of through-holes that define the walls of the well and a plate bottom that is sealed against said plate top and defines the well floors. Optionally, the plate bottom provides conductive electrode surfaces that are exposed to the interior volume of the wells and may be used as electrodes in electrochemical assays or electrochemiluminescence assays.

A multi-well plate is provided comprising
a) a plate body with a plurality of wells defined therein including:
 i) a plurality of assay wells comprising a dry assay reagent; and
 ii) a plurality of desiccant wells comprising a desiccant, and
b) a plate seal sealed against said plate body thereby isolating said plurality of wells from the external environment.

The plate is optionally, arranged so that the wells are in a standard well arrangement (e.g., 4×6, 8×12, 16×24 or 32×48 arrays of wells arranged in a square lattice). Suitable configurations of assay wells include, but are not limited to, wells with dry reagents (e.g., capture and/or detection reagents) as described in the embodiments described above.

Advantageously, the desiccant wells may be connected by drying conduits to the assay wells, the conduits permitting diffusion of water vapor from the assay wells to the desiccant wells but intersecting the wells at a height in the assay well above the location of the dry assay reagent. In one embodiment, such conduits may be provided by sealing the plate seal against recessed channels in the top surface of the plate body that connect assay wells to desiccant wells. In certain embodiments, the wells of said plate are divided into a plurality of assay panels comprising at least one assay well and at least one dessicant well. In these embodiments, the wells in an assay panel are interconnected via drying conduits but are not connected to wells in other assay panels. In one specific embodiment, an assay panel comprises one assay well and one desiccant well.

In one embodiment of a multi-well plate with assay wells and desiccant wells, the assay well comprises a binding surface having a capture reagent immobilized thereon and a reconstitutable dry labeled detection reagent. The assay well may further comprise one or more additional immobilized capture reagents, the capture reagent and additional capture reagents forming a patterned array of binding domains on said binding surface, the binding domains differing in specificity or affinity for binding partners. In addition, the reconstitutable dry reagent may further comprise one or more additional labeled detection reagents, the detection reagent and additional detection reagents differing in specificity or affinity for binding partners. Optionally, the binding surface is suitable for use as an electrode in an electrochemiluminescence assay.

In certain embodiments of a multi-well plate with assay wells and desiccant wells, the plate body is a one-piece injection-molded part. Alternatively, the plate body may comprise a plate top having a plurality of through holes that define well walls and plate bottom that is sealed against said plate top and defines well floors. Said through holes and plate bottom may define all the wells or on only a portion of the wells, e.g., only said assay wells or only said desiccant wells. The plate bottom may, optionally, provide conductive electrode surfaces that are exposed to the interior volume of the wells.

A multi-well plate is also provided comprising
  a) a plate body with a plurality of wells defined therein containing a dry assay reagent, said plate body comprising a plate top having a plurality of through-holes that define well walls and a plate bottom that is sealed against said plate top and defines well floors,
  b) a plate seal sealed against said plate body, thereby isolating said plurality of wells from the external environment, and
  c) a dessicant material.

The plate is optionally, arranged so that the wells are in a standard well arrangement (e.g., 4×6, 8×12, 16×24, or 32×48 arrays of wells arranged in a square). The plate bottom may, optionally, provide conductive electrode surfaces that are exposed to the interior volume of the wells. Suitable configurations of assay wells include, but are not limited to, wells with dry reagents (e.g., capture and/or detection reagents) as described in the embodiments above. In certain embodiments, the desiccant is comprised in the plate seal, a gasket layer between the plate seal and the plate top, the plate top, a gasket layer between the plate top and plate bottom and/or the plate bottom. For example, the desiccant may be impregnated in these components or in a coating on these components, etc. Alternatively, the plate body may define one or more additional wells that hold the desiccant.

In one embodiment, the assay well comprises a binding surface having a capture reagent immobilized thereon and a reconstitutable dry labeled detection reagent. Optionally, the binding surface is suitable for use as an electrode in electrochemical or electrochemiluminescence assays. The assay well may further comprise one or more additional immobilized capture reagents, the capture reagent and additional capture reagents forming a patterned array of binding domains on said binding surface that differ in specificity or affinity for binding partners. In addition, the reconstitutable dry reagent may further comprise one or more additional labeled detection reagents, the detection reagent and additional detection reagents differing in specificity or affinity for binding partners.

BRIEF DESCRIPTION OF DRAWINGS

FIGS. 1a-1e show non-scale schematic views of several embodiments of multi-well plate wells that include dry reagents.

FIGS. 2a-2j show non-scale schematic top and cross-sectional views of several embodiments of wells having walls with shelf elements including ledges (FIGS. 2a-2f), bridges (FIGS. 2g-2h) and tables (FIGS. 2i-2j) that may be used to support dry reagents.

DESCRIPTION OF SPECIFIC EMBODIMENTS OF THE INVENTION

Figure 3A:
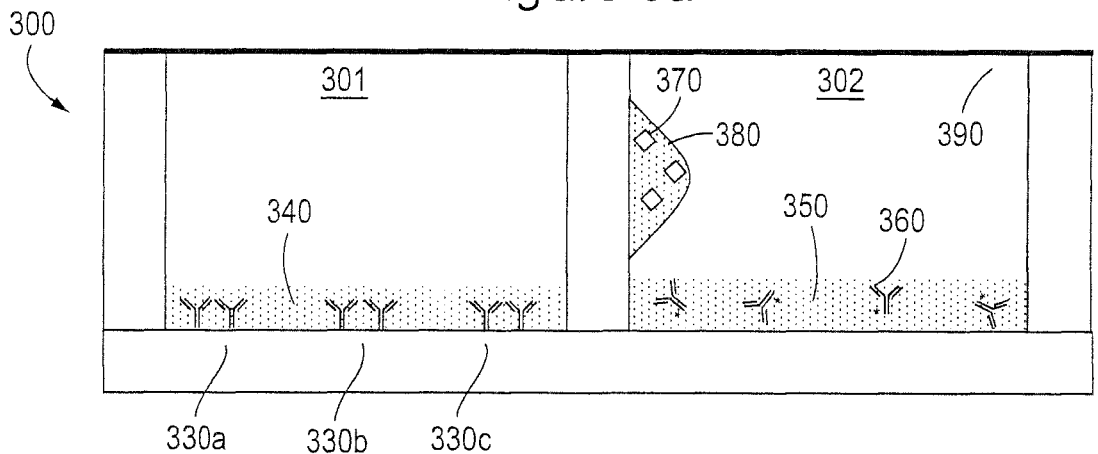
FIGS. 3a-3c show schematic illustrations of multi-well plates having detection wells and reagent reconstitution wells.

We describe assay modules (for example, assay plates, cartridges, multi-well assay plates, reaction vessels, etc.) having assay reagents pre-loaded in the wells, chambers, or assay regions of the assay module. In certain embodiments, these assay reagents are stored in a dry state. Furthermore, the assay modules may comprise desiccant materials for maintaining the assay reagents in a dry state. The assay modules preloaded with the assay reagents can greatly improve the speed and reduce the complexity of assay measurements while maintaining excellent stability during storage. We also describe methods for making such assay modules and methods for using the assay modules in assays.

The dried assay reagents may be any assay reagent that can be dried and then reconstituted prior to use in an assay.

These include, but are not limited to, binding reagents useful in binding assays, enzymes, enzyme substrates, indicator dyes and other reactive compounds that may be used to detect an analyte of interest. The assay reagents may also include substances that are not directly involved in the mechanism of detection but play an auxiliary role in an assay including, but not limited to, blocking agents, stabilizing agents, detergents, salts, pH buffers, preservatives, etc. Reagents may be present in free form or supported on solid phases including the surfaces of compartments (e.g., chambers, channels, flow cells, wells, etc.) in the assay modules or the surfaces of colloids, beads, or other particulate supports. In certain embodiments, a dry reagent (e.g., a reconstitutable dry reagent) is included that comprises ammonium phosphate as a buffering component, comprises other ammonium salts, and/or comprises less than about 1% (w/w) or less than about 0.1% (w/w) of sodium or potassium ions.

Many of the embodiments will be described in the context of multi-well plates holding dry capture and detection reagents for binding assays where the capture and detection reagents are stored on the plate in a manner that prevents them from contacting each other. But it will be clear to the skilled artisan that such embodiments can be more generally applied to the storage of any number of different dry assay reagents (whether they are binding reagents, immobilized or not, labeled or not, etc.) in a manner that prevents them from contacting each other prior to use. Likewise, while many of the drawings use a "Y" symbol to represent reagents or binding reagents, the use of this symbol should not be interpreted as limiting these reagents to antibodies unless specifically stated. It will also be clear that the embodiments can be more generally applied to assay reagents stored in other types of assay modules in compartments other than wells (e.g., chambers, channels, flow cells, etc.).

The descriptor "reconstitutable dry" may be used to refer to dry reagents as in reconstitutable dry reagents with labeled detection reagents or dry reconstitutable protective layers, etc. This terminology is used to refer to dry reagents that are reconstituted by the addition of a sample or solvent to form a solution or suspension. Preferably, they are water-soluble or otherwise reconstitutable by addition of an aqueous sample. By comparison, an "immobilized" reagent, as the term is used herein, refers to the reagent that will normally remain on a surface after addition of a sample during the conduct of an assay, although there may be specific conditions that can be used to actively dissociate it from the surface.

Reconstitutable dry reagents may be prepared in situ in a compartment of an assay module (e.g., in the well of a multi-well assay plate). By way of example, a volume of a liquid reagent may be dispensed into the well or other compartment and dried (e.g., by air drying, vacuum drying, freeze drying, etc.) to form the reconstitutable dry reagent. By adding a small volume that remains confined on a discrete surface of the compartment (e.g., a discrete location on the bottom or wall of a well), the resulting dry reagent may remain fixedly confined to that location. Alternatively, a volume may be added that is sufficient to spread across the bottom surface or to fill the compartment/well so as to form a dry reagent layer over the contacted surfaces. Reconstitutable dry reagents may be prepared outside the assay module and added to a compartment of the module (e.g., a well of a multi-well plate) in dry form (e.g., as a dry powder or as a free-standing dry pill). Pill refers herein to a contiguous dry object such as a pressed dry tablet or a lyophilized dry bead (as in U.S. Pat. No. 5,413,732).

Some embodiments include or employ dry binding reagents that are useful in carrying out binding assays. Binding reagents that can be used in the assay modules and methods include, but are not limited to, antibodies, receptors, ligands, haptens, antigens, epitopes, mimitopes, aptamers, hybridization partners, and intercalaters. Suitable binding reagent compositions include, but are not limited to, proteins, nucleic acids, drugs, steroids, hormones, lipids, polysaccharides, and combinations thereof. Nucleic acids and proteins (in particular, antibodies) have proven especially useful in binding assays. The skilled artisan will be able to identify appropriate binding reagents for a specific application. As used herein, the term "antibody" includes intact antibody molecules (including hybrid antibodies assembled by in vitro re-association of antibody subunits), antibody fragments and recombinant protein constructs comprising an antigen binding domain of an antibody (as described, e.g., in Porter & Weir, *J. Cell. Physiol.*, 67 (Suppl. 1):51-64, 1966 and Hochman et al. *Biochemistry* 12:1130-1135, 1973). The term also includes intact antibody molecules, antibody fragments and antibody constructs that have been chemically modified, e.g., by the introduction of a label. As used herein, the term nucleic acid will be generally applied to include not only DNA and RNA but also analogs (such as peptide nucleic acids or phosphorothioate linked nucleic acids) that can participate in specific Watson-Crick or Hoogstein hybridization reactions with DNA or RNA sequences and also includes nucleic acids and analogs that have been chemically modified, e.g., by the introduction of a label.

The term "capture reagent" is used herein to refer to binding reagents that are immobilized on surface to form a binding surface for use in a solid phase binding assay. The assay modules and methods may also employ or include another binding reagent, "the detection reagent" whose participation in binding reactions on the binding surface can be measured. The detection reagents may be measured by measuring an intrinsic characteristic of the reagent such as color, luminescence, radioactivity, magnetic field, charge, refractive index, mass, chemical activity, etc. Alternatively, the detection reagent may be labeled with a detectable label and measured by measuring a characteristic of the label. Suitable labels include, but are not limited to, labels selected from the group consisting of electrochemiluminescence labels, luminescent labels, fluorescent labels, phosphorescent labels, radioactive labels, enzyme labels, electroactive labels, magnetic labels and light scattering labels.

Assays that may be carried out include "sandwich assays" that employ an immobilized capture reagent and a detection reagent that can bind simultaneously to an analyte of interest so as to have the effect of sequestering the detection reagent on the binding surface. Thus, the presence of the analyte can be measured by measuring the accumulation of the detection reagent on the surface. Assays may also include "competitive assays" that i) employ an immobilized capture reagent that competes with an analyte for binding to a detection reagent or ii) a detection reagent that competes with an analyte for binding to an immobilized capture reagent. In the case of the competitive assay, the presence of analyte leads to a measurable decrease in the amount of detection reagent on the binding surface.

Capture or detection reagents may directly bind to (or compete with) an analyte of interest or may interact indirectly through one or more bridging ligands. Accordingly, the dry assay reagents may include such bridging ligands. By way of example, streptavidin or avidin may be used as capture or detection reagents by employing biotin-labeled bridging reagents that bind or compete with the analyte of interest. Similarly, anti-hapten antibodies may be used as capture or detection reagents by employing hapten labeled binding reagents that bind or compete with the analyte of interest. In another example, anti-species antibodies or Fc receptors (e.g., Protein A, G or L) are used as capture or detection reagents through their ability to bind to analyte specific antibodies. Such techniques are well established in the art of binding assays and one of average skill in the art will be able to readily identify suitable bridging ligands for a specific application.

Certain embodiments of the assay modules/plates include a capture reagent immobilized on a surface of the module/plate so as to form a binding surface. Immobilization may be carried out using well established immobilization techniques in the art of solid phase binding assays such as the techniques that have been established for carrying out ELISA assays or array-based binding assays. In one example, binding reagents may be non-specifically adsorbed to a surface of a well of a multi-well plate. The surface may be untreated or may have undergone treatment (e.g., treatment with a plasma or a charged polymer) to enhance the adsorbance properties of the surface. In another example, the surface may have active chemical functionality that allows for covalent coupling of binding reagents. After immobilizing the reagent, the surface may, optionally, be contacted with a reagent comprising a blocking agent to block uncoated sites on the surface. For conducting multiplexed measurements, binding surfaces with arrays of different capture reagents may be used. A variety of techniques for forming arrays of capture reagents are now well established in the art of array based assays.

The binding surfaces are, optionally, coated with a reconstitutable dry protective layer. The protective layer may be used to stabilize a binding surface, to prevent a binding surface from contacting detection reagents during manufacture or storage, or simply as a location to store assay reagents such as bridging reagents, blocking reagents, pH buffers, salts, detergents, electrochemiluminescence coreactants, etc. Stabilizers that may be found in the protective layer include, but are not limited to, sugars (sucrose, trehalose, mannitol, sorbitol, etc.), polysaccharides and sugar polymers (dextran, FICOLL, etc.), polymers (polyethylene glycol, polyvinylpyrrolidone, etc.), zwitterionic osmolytes (glycine, betaine, etc.) and other stabilizing osmolytes (trimethylamine-N-oxide, etc.). Blocking agents are materials that prevent non-specific binding of assay components, especially detection reagents, to binding surfaces and include proteins (such as serum albumins, gamma globulins, immunoglobulins, dry milk or purified casein, gelatin, etc.), polymers (such as polyethylene oxide and polypropylene oxide) and detergents (e.g., classes of non-ionic detergents or surfactants are known by the trade names of BRIJ, TRITON, TWEEN, THESIT, LUBROL, GENAPOL, PLURONIC, TETRONIC, and SPAN). In certain embodiments, a protective layer is included that comprises ammonium phosphate as a buffering component, comprises other ammonium salts, and/or comprises less than 1% or 0.1% (w/w) sodium or potassium ions.

One embodiment is a multi-well plate comprising at least one well having (1) a first dry assay reagent and (2) a second dry assay reagent wherein one or both of said first and second dry reagents is a reconstitutable dry reagent and wherein said first and second dry reagents do not contact each other. The well may further include one or more additional dry reagents. These may include one or more additional reconstitutable dry reagents that do not contact the first and/or second dry reagents. The embodiment also includes methods for conducting assays in these plates for an analyte of interest comprising adding liquid samples to one or more wells of a plate, reconstituting reconstitutable dry reagents in the wells and measuring an analyte-dependent assay signal so as to measure analyte in the sample. The skilled artisan will be able to readily select reagents and detection methodology for measuring a wide variety of analytes based on knowledge in the assay art. Detectable signals that may be measured include, but are limited to, optical absorbance, photoluminescence (e.g., fluorescence), chemiluminescence, electrical current or potential, catalytic activity, chemical activity, light scattering, agglutination, radioactivity, electrochemiluminescence, magnetism, changes in refractive index, and other signals that have been used in assay measurements.

Another embodiment is a multi-well plate comprising at least one well having (1) a binding surface having a first binding reagent immobilized thereon and (2) at least one additional dry reagent, wherein at least one additional dry reagent is a reconstitutable dry reagent that does not contact the binding surface. The multi-well plate may have an electrode surface with a binding surface incorporated in at least one well of the multi-well plate.

FIGS. 1a-1e show non-scale schematic views of several embodiments of well 100 of a multi-well plate. The well is defined by well floor 120 and well walls 110. Floor 120 and walls 110 may be formed of a single contiguous material or may be separate components (e.g., a plate top and plate bottom) that are mated together. Well 100 also contains a first dry reagent 130 located on floor 120 that, as shown, may be one or more capture reagents that are immobilized on floor 120 to form a binding surface. First dry reagent 130 may include a plurality of immobilized capture reagents (e.g., reagents 130a, 130b, and 130c) that are patterned into a plurality of discrete binding domains (e.g., an array). Advantageously, the binding reagents/domains may have different affinity or specificity for binding partners; such binding domains may be used to carry out multiplexed array-based measurements. A reconstitutable protective layer 140 covers dry reagent 130. Protective layer 140 may be omitted, e.g., when it is not required to physically separate reagents 130 and 150. Well 100 also comprises a second dry reagent 150 that is a reconstitutable dry reagent. Second dry reagent 150 may comprise a detection reagent such as labeled detection reagent 160. Optionally, second dry reagent 150 comprises a plurality of detection reagents that differ in affinity or specificity for binding partners. Well 100 may also include an, optional, additional reconstitutable dry reagent 170 that comprises an assay control analyte 180 (as shown in FIGS. 1c-1e). Also shown is plate seal 190. Plate seal 190, which may be omitted, is sealed against the top surface of walls 110 to protect the dry reagents from the environment.

FIG. 1a shows an embodiment in which first dry reagent 130 is coated with reconstitutable protective layer 140. Second dry reagent 150 is layered onto of protective layer 140 which prevents second dry reagent 150 from contacting first dry reagent layer 130. In one example of this embodiment, second dry reagent 150 is deposited by dispensing it in liquid form on protective layer 140; protective layer 140 is chosen to have enough thickness or mass such that it can adsorb this liquid without allowing it to contact dry reagent 130. The liquid is then dried to form second dry reagent 150. In an alternate example, protective layer 140 is introduced in liquid form and frozen in the well to form a first frozen layer. Reagent 150 is then introduced in liquid form and frozen as a second frozen layer over the first frozen layer. Lyophilization of the two frozen layers provides the layered dry reagent structure.

FIG. 1b shows an embodiment where reagents 130 and 150 are both fixedly located on non-overlapping regions of floor 120. Additional dry reagents, such as assay control reagents (not shown), could be located on other non-overlapping regions of floor 120. The localization of reagents on selected regions of floor 120 may be carried out using standard techniques in patterned reagent deposition or dispensing. Optionally, floor 120 has relatively hydrophilic domains surrounded by relatively hydrophobic areas such that appropriate volumes of reagents dispensed on the hydrophilic domains will spread to defined boundaries determined by the hydrophobic areas. In this and other embodiments where reconstitutable dry reagents are located on a surface, one may pre-treat the surface with blocking agents to prevent adsorption of the reagents to the surfaces and/or include blocking agents in the reagent composition.

FIG. 1c shows an embodiment where second dry reagent 150 is fixedly located, as one or more dry reagent pills, on walls 110. The pills may be formed, e.g., by dispensing one or more droplets of the reagent (in liquid form) on walls 110 and drying them to form the dry reagent pills. FIG. 1c also shows optional additional dry reagent 170 with control analyte 180 fixedly located on another non-overlapping region of walls 110. FIG. 1d shows an embodiment that is like that shown in FIG. 1c except that reagents 150 and 170 are located on shelves 115 on walls 110. Dry reagents 150 and 170 may be formed from liquid reagents by dispensing and drying them on shelves 115 or dispensing them above shelves 115 so that they run down walls 110 onto shelves 115 where they are dried. Alternatively, free-standing dry reagent pills may be placed on shelves 115.

Finally, FIG. 1e shows an embodiment where reagent 150 and optional reagent 170 are free standing dry reagent pills. Also included are embodiments of well 100 in which there is some combination of reconstitutable dry reagents on the well floor, well walls, well shelves, and/or in free-standing form. In alternate embodiments, some combination of fixedly located and free standing reconstitutable dry reagents is employed.

As shown in the embodiments in FIG. 1, the multi-well plates include those having wells with multiple, physically-distinct, dry reagents. Similarly, for carrying out different assays in different wells, there may be different dry reagents in different wells. It may be desirable, for example for QC purposes, to be sure that the correct dry reagents are present in the wells of a plate. Accordingly, the dry reagents may include indicators (such as dyes or fluorophores) that can be used in optical inspection of the plates. By using different distinguishable indicators in different dry reagents, it is possible to optically inspect a plate to ensure that the correct reagents are in the appropriate locations in the appropriate wells of a plate.

FIG. 2 shows non-scale schematic views of several embodiments of wells that have shelf elements on which liquid reagents can be held and dried and/or on which free-standing dry reagents may be supported above the well bottom. The shelf elements may include ledges, bridges or tables as described below. FIG. 2a is a cross-section of a well 200 showing well bottom 200 and well wall 210, the well wall having ledges such as ledges 230 and 235 that can support dry reagents. Ledge 230 has an angle that is substantially 90° or less than 90° relative to the wall directly above the ledge such that an appropriate volume of reagent can be dispensed on ledge 230 and accumulate on ledge 230 without overflowing onto well bottom 200. The ledges may also have additional features to help contain reagents such as lip 240 on ledge 235.

Shelf elements such as ledge 235 may be located at any height ($h_s$) above well bottom 240 ($h_b$=0) and below the height of the well ($h_w$). In some embodiments, $h_s$ is greater than or equal to 0.02 $h_w$, 0.05 $h_w$ or 0.1 $h_w$ but less than or equal to 0.1 $h_w$, 0.25 $h_w$ or 0.5 $h_w$. In other embodiments, $h_s$, is greater or equal to about 0.1 mm, 0.2 mm, 0.5 mm, or 1 mm but less than or equal to about 1 mm, 2 mm, or 5 mm. Through proper selection of shelf height and volumes of sample/reagent added during the course of an assay, it may be possible to control the order or timing of assay reactions. In one example, the shelf height and sample volume are chosen such that addition of sample to the well provides a height of liquid that contacts reagents on the bottom of the well and also reconstitutes reagents on one or more shelves. Alternatively, shelf height may be chosen so that addition of defined volume of a first liquid contacts dry reagents on the bottom of the well (reconstituting reconstitutable reagents on the bottom and/or allowing reactions to proceed involving reagents stored on the bottom) but does not reach the height of one or more shelves. Reactions involving reagents on the shelves can be commenced at a later time by adding sufficient volume of a second liquid so that the liquid level reaches the height of the shelves so as to reconstitute dry reagent on the shelves. In conducting an assay, the sample to be measured may be the first liquid, second liquid or both.

FIGS. 2b-2f show top views of several embodiments of well 200 and show that the well openings may have a variety of shapes including, but not limited to, square (FIGS. 2b-2d) and round (FIGS. 2e-2f). Furthermore, the shelf elements may extend around the perimeter of the well as in FIGS. 2b and 2e or there may be one or more isolated shelf elements that only extend partially around the well as in FIGS. 2c-2d and 2f A well may also include a plurality of shelf elements at different heights within a well. FIGS. 2g-2h show cross-section and top views, respectively, of a well 290 in which a shelf element is provided by bridge 250 that extends across the well. FIGS. 2i-2j show cross-section and top views, respectively of a well 295 in which a shelf element I provided by a table 260 that extends vertically from an area of well bottom 220.

A multi-well plate is provided comprising a plate body with a plurality of wells defined therein including: a) a plurality of first reagent wells holding a reconstitutable first dry reagent and b) a plurality of second reagent wells holding a second dry reagent (which may be a reconstitutable dry reagent or an immobilized reagent), wherein, the first and second reagents are matched reagents for conducting an assay (i.e., they are both used in conducting an assay of interest). The reagents may be located in a variety of locations with the wells such as well bottom, well walls, on shelf elements, as free-standing pills or powders, etc. A method is provided for carrying out assays in these plates comprising: a) adding a sample to one of the first reagent wells, b) reconstituting reconstitutable dry labeled detection reagents in the first reagent well to form a reaction mixture, c) transferring an aliquot of the reaction mixture to one or more of the second reagent wells, and d) incubating the reaction mixture in the second reagent well(s) so as to carry out said assay on said sample. In one embodiment, the multi-well assay plate can be divided into a plurality of sets of wells consisting of one first reagent well and one or more second reagent wells and the method further comprises repeating the process of (a)-(d) for each set of wells.

FIG. 3a is a (not to scale) schematic illustration of one embodiment showing cross-sectional views of two wells of a multi-well plate 300. Well 302 is a reagent reconstitution well comprising one or more reconstitutable dry reagents which may include a labeled detection reagent (such as dry reagent 350 comprising labeled detection reagent 360) or a an assay control analyte (such as dry reagent 370 comprising assay control analyte 380). These dry reagents may include additional reagent components such as blocking agents, stabilizers, preservatives, salts, pH buffers, detergents, bridging reagents, ECL coreactants and the like. The reagents may be located on well bottoms, specific locations on well bottoms, on well walls, shelf elements or may be free-standing (as per the discussion of FIGS. 1 and 2). Well 301 is a detection well comprising one or more dry reagents which may include reconstitutable dry reagents or an immobilized dry reagent. As shown, well 301 comprises immobilized capture reagents 330 that are patterned into three binding domains 330a, 330b, and 330c to form a binding surface. Well 301 also comprises a reconstitutable protective layer 340 which may be omitted. In one embodiment of an assay, sample is added to the reagent reconstitution well where reconstitutable dry reagents are reconstituted. The sample is then transferred to the detection well where the assay measurement is carried out. Alternatively, a reconstitution buffer may be used to reconstitute reagents in the reagent reconstitution well; the reconstitution buffer is then combined with sample in the detection well. FIG. 3a also shows plate seal 390 which seals against the openings of wells 301 and 302 to protect the contents of the wells from the environment.

Figure 3B:
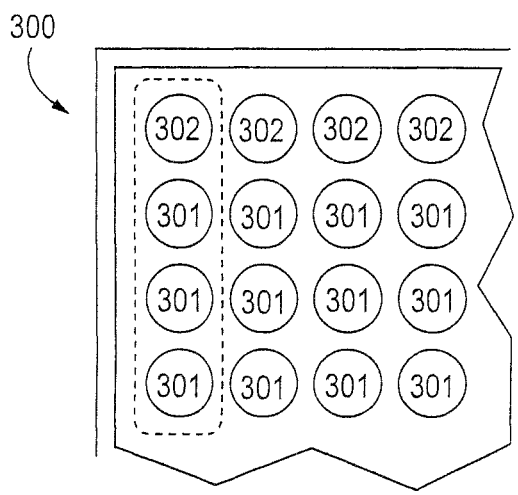
Figure 3C:
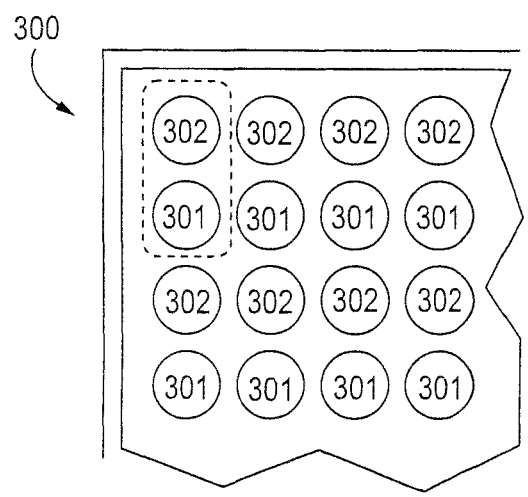

The detection and reagent reconstitution wells in a multi-well plate may be grouped into a plurality of assay sets consisting of one reagent reconstitution well and one or more detection wells, the reagent reconstitution well and detection wells within a set comprising matched capture and detection reagents for measuring an analyte of interest. FIG. 3b shows an arrangement where a set has one reagent reconstitution wells 302 and three detection wells 301. During an assay, a sample added to well 302 may then be distributed among the three associated detection wells 301 so as to conduct multiple replicates or, where the detection wells hold different reagents, multiple different assays. FIG. 3c shows an arrangement where a set has one reagent reconstitution well 302 and one detection well 301.

Figure 4A:
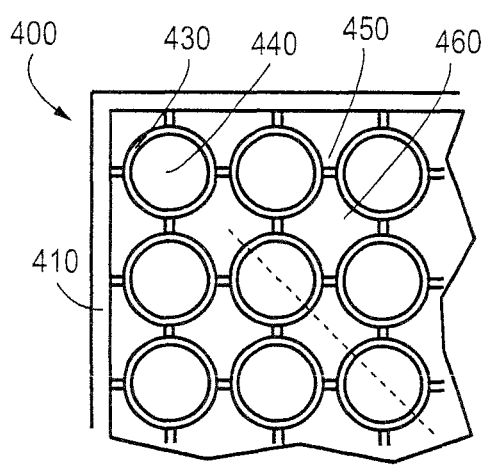
FIGS. 4a-4b show top and cross-sectional schematic views of one embodiment of a plate having detection wells and reagent reconstitution wells, the reagent reconstitution wells being located in interstitial spaces between the detection wells.
Figure 4B:
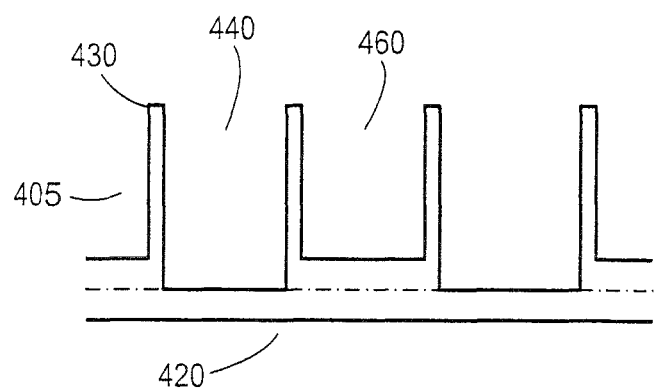

Reagent reconstitution wells and detection wells may be similar in size and shape or may have different sizes and/or shapes. In some embodiment, the wells in a standard multi-well plate are divided between the two types of wells. FIG. 4 shows a non-scale schematic views of an alternative arrangement of wells. FIG. 4a shows a top view of multi-well plate 400 having detection wells 440 that are arranged in a regular two dimensional pattern and that have detection wells walls 430 with inner wall surfaces and outer wall surfaces. Multi-well plate also has reagent reconstitution wells 460 in interstitial spaces between detection wells. Reagent reconstitution wells 460 have well walls that are defined by the outer well surfaces of detection well walls 430 and rib elements 450 that connect the outer surfaces of well walls 430 of adjacent detection wells (and, in the outermost of the wells, by the inner surface of plate frame wall 410). As shown, the detection wells may be shaped to have no reentrant (i.e., inward pointing) curves or angles while the interstitial wells may have reentrant curves and/or angles. FIG. 4b shows a cross-sectional view along the dotted line in FIG. 4a and shows the bottom surfaces of the two types of wells (which may be at different heights in the plate body). Plate 400 may be formed from a single contiguous material. In an alternate embodiment, plate 400 is formed from a plate top 405 and a plate bottom 420 that are mated along the dotted line shown in FIG. 4b. Advantageously, the basic arrangement of arrays of round wells with interstitial wells defined by the well walls and rib elements is a common feature of many injection-molded 96-well plates and plate tops and allows these components to be used to form dry reagent plates as shown in FIG. 4.

A multi-well plate is provided comprising a) a plate body with a plurality of wells defined therein including: i) a plurality of assay wells comprising a dry assay reagent; and ii) a plurality of desiccant wells comprising a desiccant, and b) a plate seal sealed against said plate body thereby isolating said plurality of wells from the external environment. In some embodiments, the assay wells comprise the necessary reagents for conducting an assay in the assay well. Also included are embodiments in which the desiccant wells are connected by drying conduits to the assay wells, the conduits permitting diffusion of water vapor from the assay wells to the desiccant wells but intersecting the wells at a height in the assay well above the location of the dry assay reagent. In addition to multi-well plates containing dry reagents and desiccants, the plates themselves (i.e., without dry reagents and desiccants), in particular, plates having conduit or channel elements (e.g., as shown in FIG. 5 described below) that are suitable for connecting sets of desiccant and assay wells with dry reagents are provided.

FIG. 5 shows non-scale schematic views of a multi-well plate 500 having assay wells 501 and desiccant wells 502 (desiccant and dry reagents are not shown). FIG. 5a is a top view showing well walls 510 and conduits 508 connecting dessicant wells with one (e.g., as in row A) or more assay wells (e.g., as in row B). FIG. 5b shows a cross-sectional view along the dotted line in FIG. 5a and together with FIG. 5a shows how conduits 508 may be formed by sealing plate seal 515 against channels in the top surface of the plate body. Plate seal 515 seals against these channels and the tops of the wells to form sets of assay and dessicant wells that are interconnected by conduits but are isolated from the environment and from other sets of wells. Accordingly, one or more sets of wells may be unsealed and used in an assay and the remaining sets of wells will be maintained in a dry environmentally protected environment. Plate 500 may be formed from a single contiguous material. In an alternate embodiment, plate 500 is formed from a plate top 505 and a plate bottom 512 that are mated along the dotted line shown in FIG. 5b, plate bottom 512 defining the floor of at least some of the wells.

The assay wells or sets of wells in plate 500 may include one or more of any of the dry reagent-containing wells described above, for example, in the descriptions of FIGS. 1-4 and may include both detection wells and reagent reconstitution wells. The desiccants used in the desiccant well may be selected from known desiccant materials including, but not limited to, silica, activated alumina, activated clays, molecular sieves and other zeolites, hydroscopic salts (e.g., anhydrous calcium sulfate, magnesium sulfate, sodium sulfate, sodium hydroxide and lithium chloride), hydroscopic solutions (e.g., concentrated solutions of lithium chloride) and water reactive materials such as phosphorous pentoxide. In some embodiments, the desiccant is present as a free dry powder or granular material. In other embodiments, the desiccant is present as a dry pill, for example a pressed tablet or a desiccant impregnated polymeric material. In other embodiments, the desiccant is contained in a water vapor permeable bag or container (e.g., as in commercial silica pouches). Advantageously, desiccant in pill form or pre-packaged containers may be "press fit" into desiccant wells to prevent movement in the well during shipping or use.

Figure 5A:
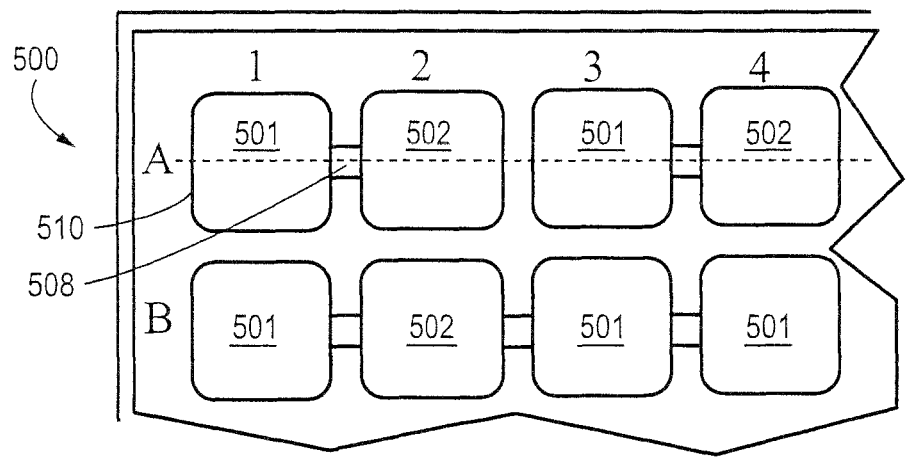
FIGS. 5a-5f show schematic views of multi-well plates 500 (FIGS. 5a-5b), 520 (FIGS. 5c-5d) and 540 (FIGS. 5e-5f) having assay wells and desiccant wells.
Figure 5B:
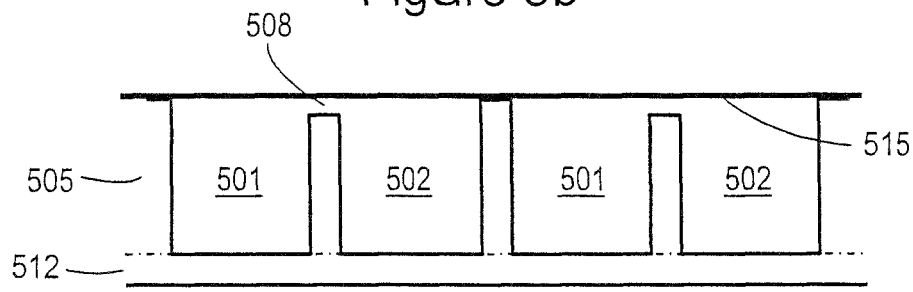
Figure 5C:
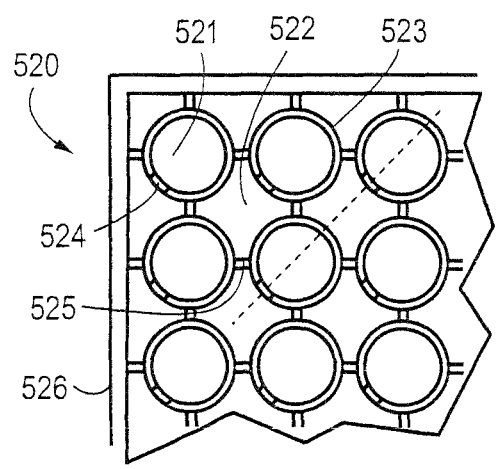
Figure 5D:
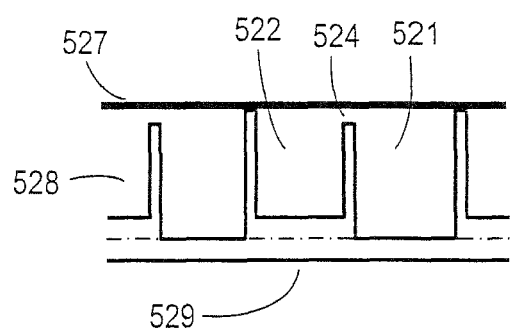

FIGS. 5c-5d show top and cross-sectional views of one embodiment of a multi-well plate 520 with assay and desiccant wells. Plate 520 has assay wells 521 (which may contain dry assay reagents) that are arranged in a regular two dimensional pattern and that have assay well walls 523 with inner wall surfaces and outer wall surfaces. It also has desiccant wells 522 in interstitial spaces between detection wells (alternatively, wells 521 are used as desiccant wells and wells 522 are used as assay wells). Desiccant wells 522 have well walls that are defined by the outer well surfaces of detection well walls 523 and rib elements 525 that connect the outer surfaces of well walls 523 of adjacent assay wells (and, in the outermost of the wells, by the inner surface of plate frame wall 526). Channels 524 notched into the top of well walls 523 provide, when mated to a plate seal, paths for water vapor to travel from assay wells to desiccant wells. As shown, the assay wells may be shaped to have no reentrant (i.e., inward pointing) curves or angles while the interstitial wells may have reentrant curves and/or angles. FIG. 5d shows a cross-sectional view along the dotted line in FIG. 5c and shows plate seal 527 which is mated to the top of the plate to form sets of assay and desiccant wells that are connected via conduits 524 but isolated from other wells and from the environment. Plate 520 may be formed from a single contiguous material. In an alternate embodiment, plate 520 is formed from a plate top 528 and a plate bottom 529 that are mated along the dotted line shown in FIG. 5d.

Figure 5E:
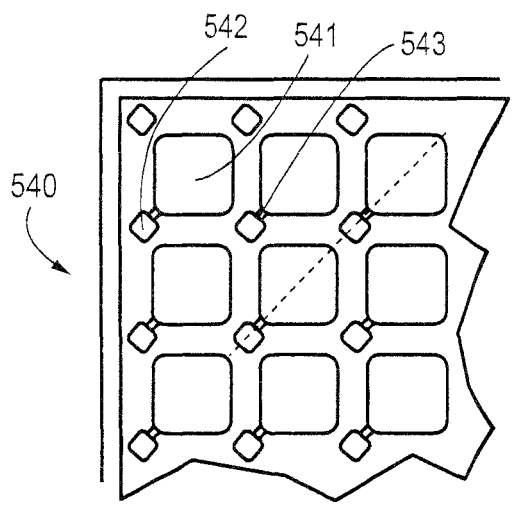
Figure 5F:
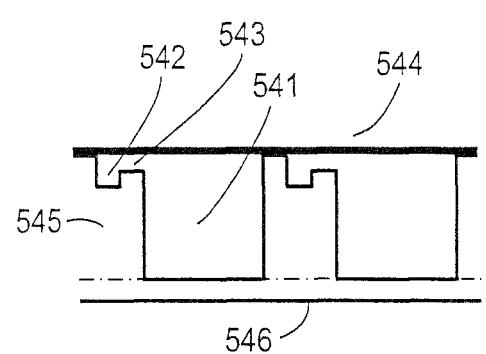

FIG. 5e shows a schematic view of another embodiment of a multi-well plate with assay wells (which may contain dry reagents) and desiccant wells and shows a plate 540 with assay wells 541 and desiccant wells 543 that are connected into sets of wells via channels 542 in the plate body. Multi-well plate 540 is largely analogous to the embodiment of plate 500 pictured in FIGS. 5a-5b except that in plate 540, desiccant wells 542 are much shallower and smaller in area than the assay wells allowing a larger portion of the plate footprint to be dedicated to wells used in assay measurements. FIG. 5f shows a cross-sectional view along the dotted line in FIG. 5e and also shows plate seal 544 that is sealed against the top of the plate to form connected sets of assay and desiccant wells. Plate 540 may be formed from a single contiguous material. In an alternate embodiment, plate 540 is formed from a plate top 545 and a plate bottom 546 that are mated along the dotted line shown in FIG. 5f; plate bottom 546 also defining the floor of assay wells 541.

Figure 6:
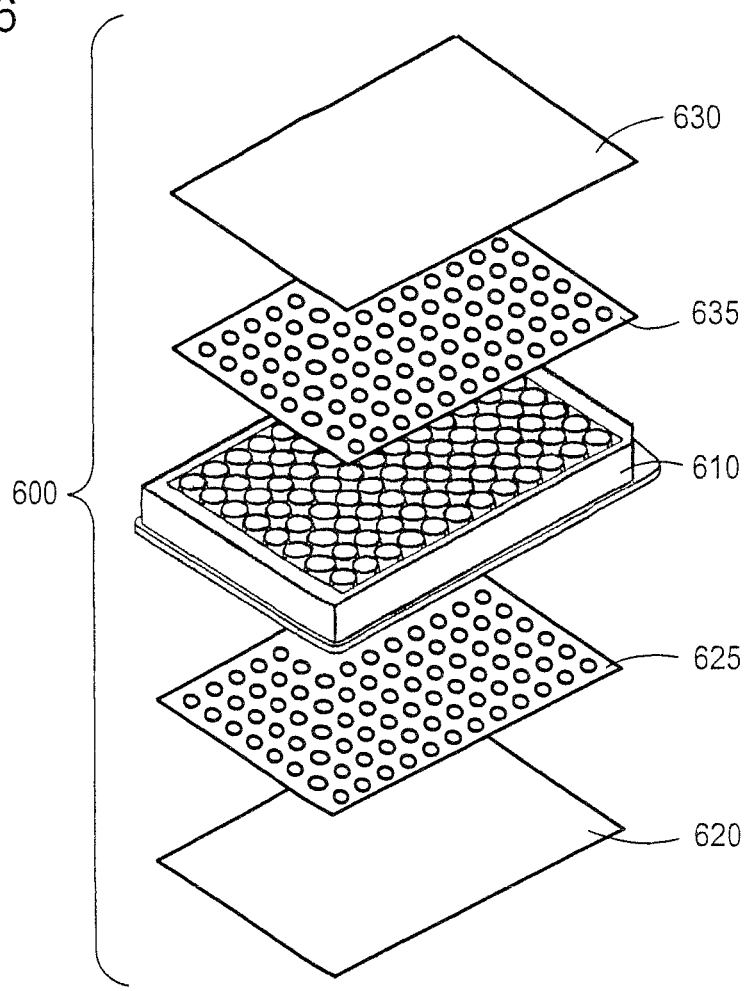
FIG. 6 is a schematic exploded view of one embodiment of a multi-well assay plate.

FIG. 6 is a schematic exploded view of one embodiment of a multi-well assay plate. Multi-well assay plate 600 comprises a plate top 610 with through-holes 615 that define the walls of wells. Plate top 610 is sealed against plate bottom 620 through gasket 625 such that plate bottom 620 defines the bottom surface of the wells. Optionally, plate top 610 is sealed directly to plate bottom 620 and gasket 625 is omitted. Sealing may be accomplished through traditional sealing techniques such as adhesives, solvent welding, heat sealing, sonic welding and the like. In another optional embodiment, plate top 610 fully defines the sides and bottom of the wells and plate bottom 620 and gasket 625 may be omitted. The contents of the wells, which may include wells configured to contain dry reagent and/or desiccant as described above, may be protected from the outside environment by sealing (e.g., via traditional sealing techniques) plate seal 630 to plate top 610 directly or via optional gasket 635.

The components of plate 600 may be made from a variety of different materials including, but not limited to, plastics, metals, ceramics, rubbers, glasses or combinations thereof. In accordance with the requirements of the particular detection technology used with the plates, the components some or all of the components may be selected to be transparent, colored, opaque, or highly light scattering. In one embodiment, plate top 610 is an injection-molded plastic such as injection-molded polystyrene, polypropylene, or cyclic olefin copolymer (COC). Optionally, one or more of the components may be made of or comprise (for example in the form of a coating) a material that has a low water vapor transmission rate, e.g., a water vapor transmission rate less than 1 $g/m^2$ per day through a 100 um thickness. Low water vapor transmission materials include, but are not limited to, glass, metals or metal films (e.g., aluminum films), COC, polyvinylidene chloride (PvDC), polypropylene, polychlorotrifluoroethylene (PCTFE), and liquid crystal polymers (LCP).

Plate 600 may include desiccant wells as described above. Alternatively, or in addition, desiccant may be incorporated directly into plate top 610, plate bottom 620, plate seal 630, gasket 625 and or gasket 635. For example, U.S. Pat. No. 6,174,952 to Hekal et al. describes desiccant containing polymer blends that may be molded, cast into liners, or formed into films, sheets, beads or pellets.

In some embodiments, plate bottom 620 has features to facilitate the patterning of reagents on the bottom of wells (e.g., patterned hydrophilic features surrounded by hydrophobic areas) and/or conductive layers that provide electrodes that are exposed to the interior volumes of the wells of plate 600 so that electrochemical or electrode induced luminescence assays (e.g., electrochemiluminescence assays) may be carried out. Plate bottom 620 may also include electrode contacts to allow an external instrument to apply electrical potential/current to the electrodes. Suitable approaches, configurations and compositions for such features, conductive layers and electrode contacts include those described in U.S. Publications 2004/0022677 and 2005/0052646 to Wohlstadter et al. Suitable instrumentation and methods that can be used to conduct ECL measurements using assay modules include those described in U.S. Publications 2004/0022677 and 2005/0052646 of U.S. application Ser. Nos. 10/185,274 and 10/185,363, respectively; U.S. Publication 2003/0113713 of U.S. application Ser. No. 10/238,391; U.S. Publication 2005/0142033 of U.S. application Ser. No. 10/980,198; and the concurrently filed U.S. application Ser. No. 11/642,968 of Clinton et al. entitled "Assay Apparatuses, Methods and Reagents."

Figure 7A:
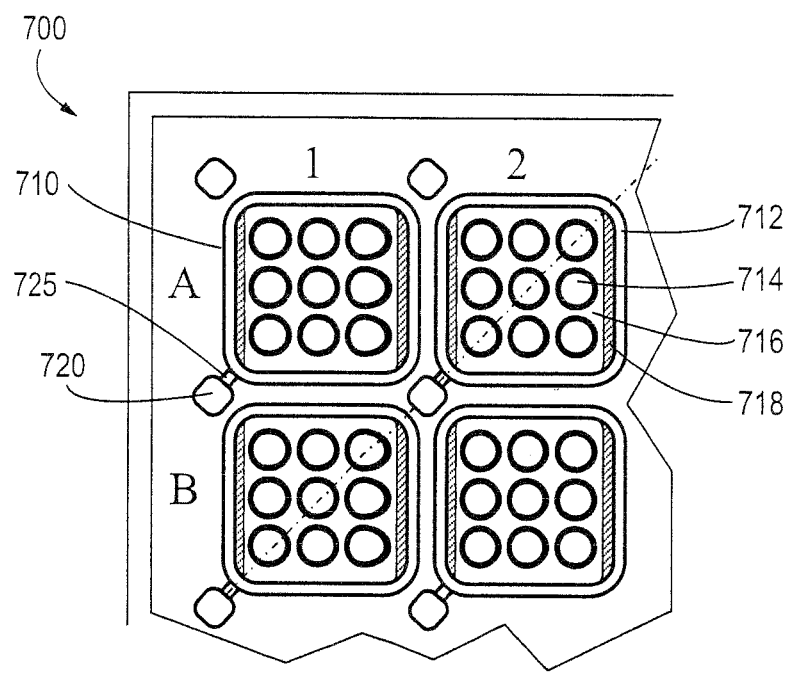
FIGS. 7a-7c show three schematic views of a multi-well plate that is configured to carry out array-based multiplexed electrochemiluminescence assays.

FIG. 7 provides schematic illustrations of one specific embodiment that includes some of the inventive concepts disclosed above in the context of a multi-well plate configured to carry out an-ay-based multiplexed electrochemiluminescence assays. FIG. 7a shows a section of multi-well plate 700 that has a plurality of assay wells 710 which may comprise dry reagents and a plurality of desiccant wells 720 which may comprise a desiccant. Channels 725 on the top surface of plate 700 link each desiccant well to an assay well. Optionally, desiccant wells 720 and channels 725 are omitted. Assay wells 710 have ledges 712 which may be used to support a reconstitutable dry reagent (e.g., dry reagents comprising assay controls and/or ECL labeled detection reagents). Assay wells also have working electrode surfaces 714 which are covered by patterned dielectric layer 716 so as to expose a plurality of exposed electrode surfaces or "spots" (shown as circles within the wells). In addition, counter electrodes 718 are provided to provide for a complete electrochemical circuit. Optionally, the surface of dielectric layer 716 is hydrophobic relative to electrode surface 714 so that small volumes of reagents patterned onto the spots may be kept confined to the spots. The different spots may have different capture reagents immobilized thereon to form a binding surface with an array of binding domains differing in specificity or affinity for binding partners (e.g., analytes of interest). Alternatively, some of the spots may have reconstitutable dry reagents confined thereon which, e.g., may contain assay controls and/or ECL labeled detection reagents. The assay well may further comprise a reconstitutable protective layer over the binding surface.

Figure 7B:
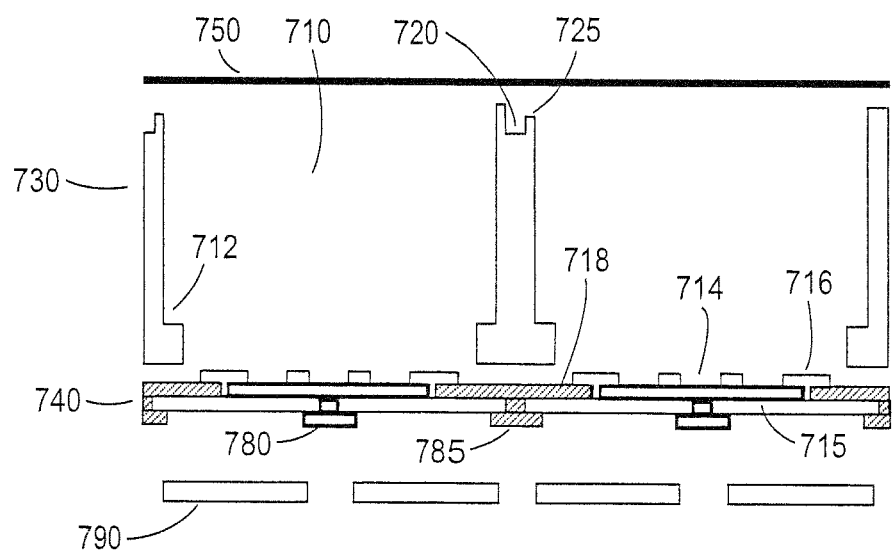

FIG. 7b provides an exploded cross-sectional view along the dotted line in FIG. 7a and illustrates one approach to forming the electrode/dielectric layers in assay wells 710. The multi-well plate comprises a plate top 730 that defines desiccant wells 720 and has through-holes that define the walls of assay wells 710 and ledges 712. Plate top 730 also has channels 725 that form conduits between assay wells 710 and desiccant wells 720 when plate seal 750 is sealed against the top surface of plate top 730. In one non-limiting example, plate top 730 is an injection-molded part molded from a plastic with low water vapor transmission. In another non-limiting example, plate seal 750 is a heat sealable film comprising a low water vapor transmission plastic or a metal (e.g., aluminum) foil.

FIG. 7b also shows plate bottom 740 which seals against plate top 730 and defines the bottom of assay wells 710. Plate bottom 740 comprises substrate 715 which supports patterned conductive layers that provide for electrodes 714 and 718. Patterned dielectric layer 716 on the electrodes defines the exposed electrode spots. A variety of materials may be used to provide for the substrate and the conductive and dielectric layers (see, e.g., U.S. Publications 2004/0022677 and 2005/0052646). In one non-limiting example, the substrate is a plastic film (made, e.g., of a polyester such as MYLAR, polyvinylchloride, or a low water vapor transmissive material such as COC), the conductive layers are screen printed conducting inks (e.g., screen printed carbon inks) and the dielectric layer is a screen printed insulating ink. Also shown in FIG. 7b are electrode contacts 780 and 785 which are conductive layers on the bottom of substrate 715 that provide connectivity (e.g., via conductive through holes in substrate 715 to electrodes 714 and 718. The electrode contacts may also be provided by screen printed conductive inks which during printing can be caused to fill holes in substrate 715 to also provide the conductive through-holes. Advantageously, the conductive through-holes may be located directly below well walls to limit water vapor transmission through the holes. In addition, an optional bottom sealing layer 790 may be sealed to the bottom of substrate 715. Bottom sealing layer 790 is made of a low water vapor transmissive material and covers most of the bottom surface of substrate 715 except for defined openings in sealing layer 790 that are located so as to allow a plate reading instrument to contact electrode contacts 780 and 785.

Figure 7C:
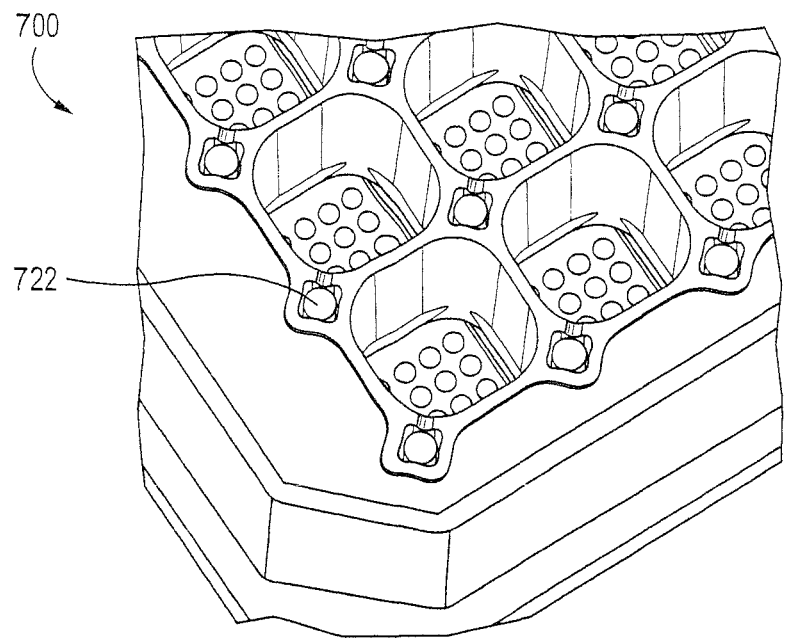

FIG. 7c shows a more detailed angled view of one embodiment of plate 700 and shows desiccant pills 722 that are press-fit into desiccant wells 720.

A variety of samples which may contain an analyte or activity of interest may be assayed. In one example, a sample is introduced to an assay plate or one or more wells of an assay plate having reconstitutable dry reagents pre-loaded thereon, thus reconstituting these assay reagents and an assay signal is measured so as to measure (quantitatively or qualitatively) the amount of analyte in the sample. The reagents may include a luminescent, electrochemiluminescent, chemiluminescent, and/or redox-active substance. Accordingly, the assay signal is preferably a luminescent or electrochemical signal. Assays formats that may be carried out include homogeneous and heterogeneous methods.

Assays that may be carried out include formats that employ solid-phase supports so as to couple the measurement of an analyte or activity to the separation of labeled reagents into solution-phase and solid phase supported portions. Examples include solid-phase binding assays that measure the formation of a complex of a material and its specific binding partner (one of the pair being immobilized, or capable of being immobilized, on the solid phase support), the formation of sandwich complexes (including a capture reagent that is immobilized, or capable of being immobilized, on the solid phase support), the competition of two competitors for a binding partner (the binding partner or one of the competitors being immobilized, or capable of being immobilized, on the solid phase support), the enzymatic or chemical cleavage of a label (or labeled material) from a reagent that is immobilized, or capable of being immobilized on a solid phase support and the enzymatic or chemical attachment of a label (or labeled material) to a reagent that is immobilized or capable of being immobilized on a solid-phase support. The term "capable of being immobilized" is used herein to refer to bridging reagents that may participate in reactions in solution and subsequently be captured on a solid phase during or prior to detection. For example, the reagent may be captured using a specific binding partner of the reagent that is immobilized on the solid phase. Alternatively, the reagent is linked to a capture moiety and a specific binding partner of the capture moiety is immobilized on the solid phase. Examples of useful capture moiety-binding partner pairs include biotin-streptavidin (or avidin), antibody-hapten, receptor-ligand, nucleic acid—complementary nucleic acid, etc.

In assays carried out on solid-phase supports, the amount of analyte or activity may be determined by measuring the amount of label on the solid phase support and/or in solution using i) a surface selective technique, ii) a solution selective technique and/or iii) after separation of the two phases. In electrochemiluminescence methods, the solid phase support may also be the working electrode used to induce electrochemiluminescence from labels bound to the solid phase. The electrochemiluminescence methods may include washing to remove unbound electrochemiluminescence labeled reagents prior to addition of an ECL coreactant (e.g., tertiary amines such as tripropylamine or piperazine-1,4-bis(2-ethanesulfonic acid)) and application of a potential to induce ECL from bound labels. Alternatively, because of the surface selectivity of electrochemiluminescence measurements, the method may be ran without washing. Advantageously, in unwashed assays, the ECL coreactant may be pre-added to assay wells in the form of a reconstitutable dry reagent or protective layer.

Another embodiment relates to kits for use in conducting assays that comprise the assay modules/multi-well plates. The kit may include one or more additional reagents in one or more containers including, but not limited to, assay calibrators, assay controls, assay diluents, ECL coreactants, and wash buffers.

According to one embodiment, the kit comprises one or more of the assay components in one or more plate wells, preferably in dry form. In one preferred embodiment, the kit comprises an assay plate having a binding immobilized on one or more working electrodes within an assay module and one or more additional assay reagents deposited in the form of a dry bead, pellet or a pill directly into the well, preferably at a position spacially separated from a working electrode, or alternatively deposited into one or more interstitial wells. Preferably, the kits do not contain any liquids in the wells.

EXAMPLES

The following examples are illustrative of some of the methods and instrumentation falling within the scope of the present invention. They are, of course, not to be considered in any way limiting of the invention. Numerous changes and modifications can be made with respect to the invention by one of ordinary skill in the art without undue experimentation.

Materials & Methods
Labeled Detection Antibodies

Labeled detection antibodies were labeled with SULFO-TAG NHS ester (Meso Scale Discovery, Gaithersburg, Md.), an electrochemiluminescent label based on a sulfonated derivative of ruthenium-tris-bipyridine (compound 1 pictured below). Labeled antibodies were purified by size exclusion chromatography on SEPHADEX G-50 (Pharmacia).

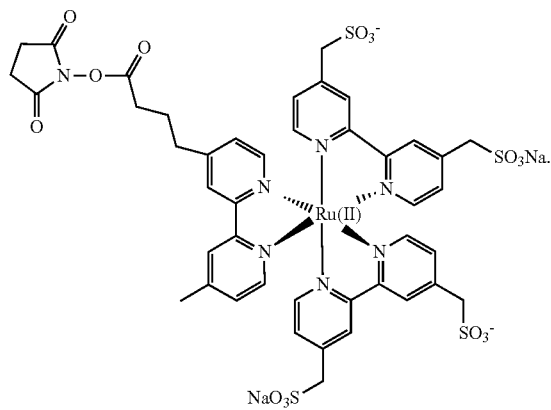

Lyophilized Detection Antibody Pills

Pills comprising one or more labeled detection antibodies were formed from a solution containing 1 µg/mL of each of the labeled antibodies, 2% bovine serum albumin and 20% sucrose in a phosphate buffered saline. Frozen droplets of this solution were formed by dispensing 20 µL droplets into liquid nitrogen. The frozen droplets were transferred onto chilled (≤−78° C.) aluminum trays which were placed on the shelves of an ADVANTAGE XL lyophilizer (Virtis). The shelves of the lyophilizer were pre-cooled to ≤−45° C. prior to introduction of the aluminum trays and a conductive paste was used to improve the heat transfer between the shelves and the trays containing beads. In a typical lyophilization protocol, the lyophilizer chamber was evacuated and the shelf temperature was slowly increased to −30° C., −20° C., −15° C. and finally to +20° C. (ambient conditions) over the course of about 24 hours. The temperature was held at each of these levels for sufficient time to allow for equilibration while controlling the chamber pressure 0.01 torr. Karl Fisher titrations of lyophilized beads typically showed water contents of less than 4% by weight. The water content could be reduced to under 2% by extended storage in the presence of a dessicant.

Multi-Well Plates for Electrochemiluminescence Measurements

Electrochemiluminescence measurements were carried out using specially designed multi-well plates having integrated screen printed carbon ink electrodes for carrying out electrochemiluminescence measurements (MULTI-ARRAY or MULTI-SPOT plates, Meso Scale Discovery, a division of Meso Scale Diagnostics, LLC, Gaithersburg, Md.). A patterned dielectric layer patterned over the working electrode on the bottom of each well exposes one or more regions or "spots" on the working electrode. In some experiments, the electrode surfaces were treated with an oxygen plasma prior to immobilizing antibodies on them. Different capture antibodies were immobilized on the different spots by patterned micro-dispensing of solutions of the antibodies on the spots using a nanoliter dispenser (Bio-Dot, Inc.). The volumes dispensed on the spots were selected so that they spread to the boundaries defined by the dielectric layers but remained confined on the spots, thus allowing for the immobilization of each antibody (via passive adsorption) on a defined region of the working electrode; if the electrode surfaces were not plasma treated, a small amount of TRI-TON X-100 detergent was added to the spotting solutions to enhance spreading. Adsorption was allowed to proceed for at least 2 hours after which the plates were washed with a stabilizing wash buffer (2% sucrose, 185 mM dibasic ammonium phosphate, 13 mM monobasic ammonium phosphate, 0.1% TWEEN 20, and KATHON CG/ICP II preservative), dried, and stored in the presence of a desiccant. By controlling the amount of wash buffer left in the wells before drying (typically between 5-20 µL), sucrose films of different thicknesses could be left over the working electrode surfaces.

Electrochemiluminescence Measurement Instrument

Electrochemiluminescence was induced and measured in the MULTI-SPOT plates using a Sector® Imager 6000 reader or a Sector® PR 400 reader (both from Meso Scale Discovery, a division of Meso Scale Diagnostics, LLC, Gaithersburg, Md.). The Sector® Imager 6000 instrument applies electrical potentials to the working electrodes in the plate and images the resultant ECL. Image analysis algorithms are employed to distinguish and quantitated the light emitted from each spot in a well. The Sector® PR 400 instrument applies electrical potential to the working electrodes in one column of the plate at a time. An array of photodiodes is used to measure the ECL emitted from the wells in the column.

Example 1. Multiplexed Cytokine Detection Using
Labeled Detection Antibodies in Lyophilized Beads High binding MULTI-SPOT plates having a 7 spot array of capture antibodies against seven different human cytokines (TNF-α, IL1-β, IL2, IL5, IL6, IL8, IL12, and GM-CSF) and lyophilized beads containing labeled detection antibodies against the same seven cytokines were prepared as described above. One bead was placed in each well and the plates were stored in the presence of dessicant until used. Multiplexed cytokine assays were carried out by introducing cytokine solutions (40 µl per well prepared in RPMI cell culture media supplemented with 10% fetal calf serum) of pre-defined concentrations into the wells of the plate and incubating for 2 hours at room temperature on a plate shaker. MSD® READ BUFFER P (Meso Scale Discovery), a solution containing a tertiary amine ECL coreactant, was added at 2× concentration to the wells (110 µl/well) and the plate was analyzed on a Sector® Imager 6000 instrument. The resultant signals on each spot showed good linearity for all seven cytokines between 10 and 10,000 pg/ml. The standard deviations of the signals were typically less than 10% of the average signals. Background signals and calculated sensitivities were similar to those obtained when the antibodies were added to the wells as liquid solutions.

Example 2. Cytokine Measurements Using a Labeled Detection Antibody that is Dried on a Protective Layer Covering a Capture Surface This assay used a small spot MULTI-ARRAY plate with a single spot per well. The spot treated, as described in the Materials and Methods section with a solution containing an anti-human TNF-α capture antibody to immobilize the antibody on the spot surface. The well was then filled with 75 µL of 4×MSD® READ BUFFER P that was supplemented with 7% FICOLL (a highly branched hydrophilic polymer of sucrose), and the plate was cooled to freezing and lyophilized overnight to provide a protective "cake" layer over the bottom of the well. A small droplet (35 nL) of a concentrated solution of a labeled anti-human TNF-α detection antibody was dispensed on the surface of the cake. The plate was then vacuum dried for 5 minutes and stored in the presence of dessicant until used. Assays were carried out by adding to the wells 150 µL of solutions containing pre-determined concentrations of human TNF-α in RPMI cell culture media supplemented with 10% fetal calf serum and shaking for two hours. The plate was then analyzed on a Sector® Imager 6000 instrument. The calculated detection limits of 5-6 pg/mL are comparable to those observed in non-washed assays using liquid detection antibody solutions.

Example 3. Cytokine Measurements Using a Labeled Detection Antibody that is Dried on the Sides of the Wells of a Multi-Well Plate This assay used a small spot MULTI-ARRAY plate with a single spot per well. The spot was coated, as described in the Materials and Methods section with an anti-human TNF-α capture antibody. Droplets (1 µL) of a 24 µg/mL solution of the detection antibody in 4.8% sucrose were dispensed on the inside walls of the wells and allowed to dry. The plates were stored in the presence of dessicant until used in an assay. The assay protocol involved adding 80 µL of a TNF-α solution to each well, shaking the plate for 30 minutes at room temperature, washing the plate, adding 150 µL of 1×MSD® READ BUFFER T (Meso Scale Discovery) and analyzing the plate on a Sector® Imager 6000 instrument. Plates stored for 18 days at room temperature or 4° C. gave detection limits that were less than 1 pg/mL and comparable to those observed in washed assays employing liquid detection antibody solutions.

Example 4. Cytokine Measurements Using a Multi-Well Plate with Wells Having a Capture Layer Coated with a Protein-Containing Protective Layer and Dried Labeled Detection Antibody on the Well Walls This assay used a MULTI-ARRAY plate with a single spot per well. The working electrode in each well was pre-coated with streptavidin (streptavidin MULTI-ARRAY plate, Meso Scale Discovery). Anti-IL1-β monoclonal antibody was immobilized on the working electrode according to the following protocol. The wells were washed three times with PBS and then treated with 20 µL of a 3 µg/mL solution of biotin-labeled anti-IL1-β. The immobilization was allowed to proceed over 2 hours under agitation on a plate shaker. The wells were then washed three times with PBS. A 20 µL volume of a buffered solution of BSA and sucrose was added to the wells and then dried in the wells under vacuum to form a dry film on the bottom of the plates.

A dry pill of SULFO-TAG labeled anti-IL1-β polyclonal antibody was formed on the well wall according to the following protocol. A 100 nL microdroplet of a 482 µg/mL solution of the labeled antibody was dispensed on each well wall using a BIO-DOT microdispensor (Bio-Dot, Inc.) with an angled tip. The droplet remained on the well wall where it was allowed to dry for 30 minutes in a dessicator chamber. The wells were then sealed with a plate heat seal. In some experiments, a low concentration of fluorescein was added to the detection antibody solution. The fluorescein fluorescence could be used to provide a quality control check by identifying any well in which the detection antibody ran down the well wall or splattered on the well bottom. The fluorescein did not affect assay performance.

Assays for IL1-β were carried out by adding 125 µL of solutions containing known amounts of IL1-β to the wells and incubating for 37 minutes while shaking the plate. The plate was then washed with PBS, MSD READ BUFFER T was added and the plate was analyzed on a Sector® PR 400 instrument. Assays using plates with dry detection antibodies performed in a comparable fashion to assays that used liquid detection antibody solutions.

Figure 8:
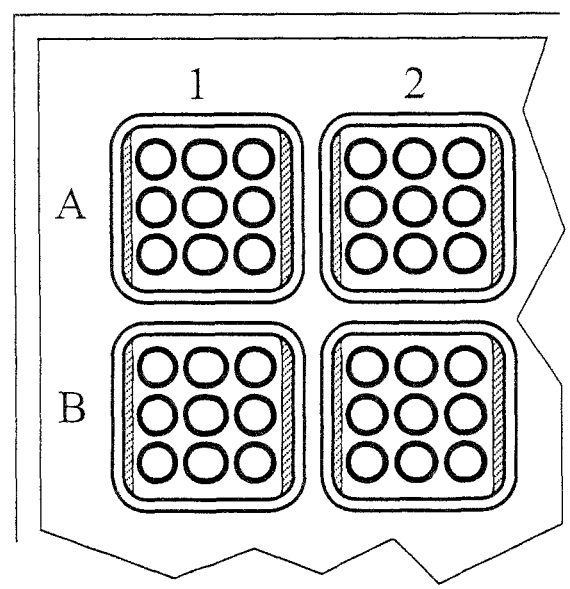
FIG. 8 shows one embodiment of a square well plate with dry reagent ledges and seven spots per well.
Figure 9:
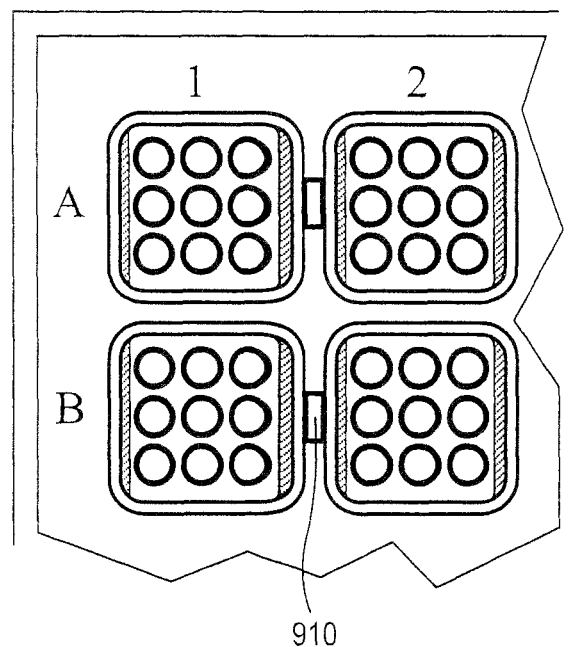
FIG. 9 shows one embodiment of a square well plate with dry reagent ledges, seven spots per well, and drying conduits between pairs of adjacent wells.
Figure 10:
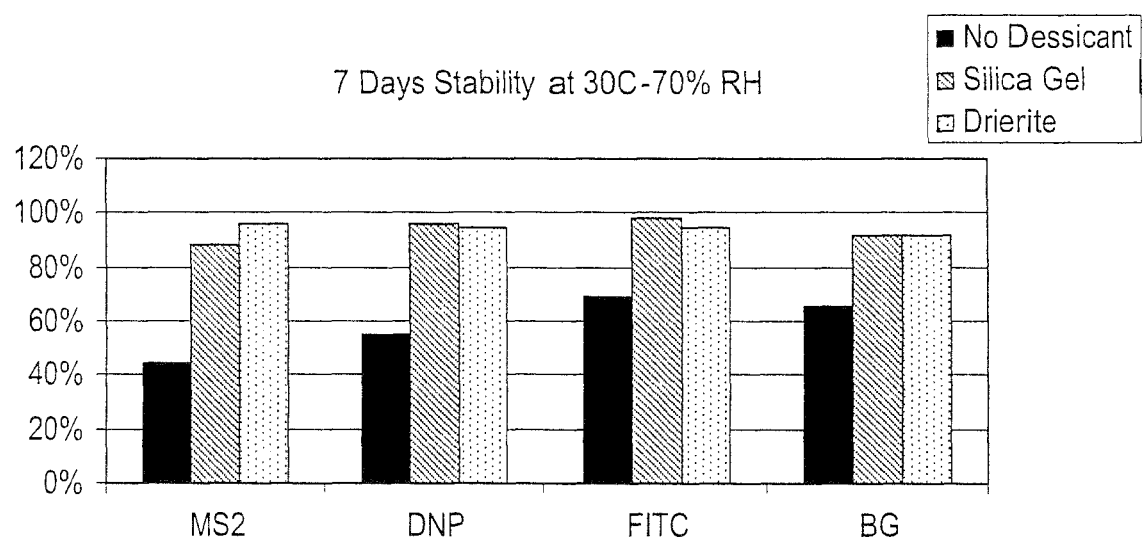
FIG. 10 shows the effect of incorporating desiccant wells into assay plates on the stability of dry reagents stored in the plates.

Example 5. Assays in Multi-Well Plates Using Dry Reagents: Storage of Dried Labeled Antibodies on Ledges in the Wells This assay used a Multi-Spot plate configured as shown in FIG. 8. The plate was similar to that shown in FIG. 7 except for the use of a 7-spot pattern and the omission of desiccant wells 720, channels 725, desiccant pills 722, and bottom sealing layer 790. The plate top was injection-molded polypropylene. Capture antibodies against were immobilized by dispensing, on the individual spots, antibodies against botulinum toxin A (BotA), dinitrophenyl (DNP), ricin, staphylococcal enterotoxin B (SEB), Venezuelen equine encephalitis (VEE), and *Yersinia pestis* (YP). Non-immune mouse IgG was immobilized on the remaining spot for use as a negative control. Immobilization was carried out by dispensing 75 nL of solutions comprising between 100-500 µg/mL of an antibody, 750 µg/mL of BSA, and 0.03% TRITON X-100. One exception was the BotA capture antibody which was biotinylated and immobilized after pre-binding it to 1200 µg/mL avidin and which was immobilized in the absence of BSA.

The non-immune IgG should not participate in a sandwich complex and should give a low signal for all samples. Elevation of this signal outside of a selected range can be used as an indication that a measurement artifact is producing elevated non-specific binding of detection antibodies and that there is a risk of false positive results. More generally, any binding reagent that is not paired with a corresponding detection reagent may be used. Optionally, the binding reagent may be selected to share structural properties with the test capture reagents, for example, in an immunoassay it may include immunoglobulins from one or more of the species from which the other capture antibodies were derived. The anti-DNP spot will be used as a positive control. The well will also include a dry SULFO-TAG labeled anti-fluorescein (FL) antibody and a defined quantity of dry BSA labeled with both DNP and FL (DNP-FL-BSA). The positive control signal should, therefore give a constant positive signal indicative of the defined quantity of DNP-FL-BSA. Reduction of this signal below a selected range can be used as an indication that a sample interferes with binding reactions or signal generation and that there is a risk of false negative results. More generally, the positive control may be an assay for any analyte that can be spiked into the reaction mixture. Preferably, there is a low likelihood of finding the analyte in the samples of interest.

The capture antibody solutions were allowed to dry for 30 minutes in a desiccated environment and then dried for 30-60 minutes under vacuum. The wells were washed with a the stabilizing wash buffer containing sucrose described in the Materials and Methods section, blocked with 5% BSA for 45 minutes and washed once more with the stabilizing wash buffer. A stabilizing/blocking solution (20 µL of 305 mM ammonium phosphate, 100 mM ammonium chloride, 0.02% TRITON X-100, 2% sucrose, 2% BSA, and 0.02% KATHON preservative, pH 7.4) was added and the solution was dried in the well under vacuum to form a dry reagent cake on the well bottom.

A mixture of STAG-labeled detection antibodies (0.5 µL of a mixture of antibodies against BotA, FL, ricin, SEB, VEE, and YP at between 40-240 µg/mL in the stabilizing/blocking solution) was dispensed (using a BIO-DOT dispenser with an angled dispense tip) on the walls of the wells just above the dry reagent ledge and allowed to flow down onto the ledge. A solution containing 80 ng/mL of the positive control analyte (DNP-FL-BSA) was dispensed on the opposite wall. The detection antibody and control solutions were allowed to dry for 30-60 minutes under vacuum. The plates were then packaged with desiccant until used.

The protocol used to conduct assays with these plates was: add 80 µL of sample (defined amounts of one or more of the target analytes in 0.1% TRITON X-100 in phosphate buffered saline (PBS)), incubate 1 hour with shaking, wash with PBS, add 150 µL 1×MSD READ BUFFER T (Meso Scale Diagnostics, LLC) and analyze plate using an MSD Sector® Imager 6000 instrument. VEE and YP used in this assay were inactivated by irradiation. BotA was used in the assay was inactivated with formalin.

The table below shows that the signals observed at each spot for samples containing no analyte (–) or for samples containing 10 ng/mL BotA, 1 ng/mL ricin, 50 ng/mL SEB, 1000 ng/mL VEE, or 10,000 CFU/mL YP. The table shows sensitive and specific detection of the target analytes and proper performance of the positive and negative control spots.

| | Capture Spot | | | | | | |
|---|---|---|---|---|---|---|---|
| Analyte | BotA | Ricin | SEB | VEE | YP | Neg | Pos |
| BotA | 28893 | 178 | 97 | 182 | 159 | 134 | 9456 |
| Ricin | 243 | 15502 | 106 | 222 | 142 | 129 | 8776 |
| SEB | 276 | 165 | 9518 | 230 | 177 | 162 | 8288 |
| VEE | 1516 | 233 | 188 | 11821 | 204 | 237 | 8506 |
| YP | 243 | 129 | 107 | 211 | 4280 | 152 | 8656 |
| — | 249 | 81 | 75 | 212 | 115 | 121 | 8923 |

The next table compares the signals observed with these plates to assays carried out under comparable conditions except for the use of liquid detection reagents. The table provides only the signal on the specific spot for a given analyte and provides both signal in the presence of analyte (10 ng/mL BotA, 1 ng/mL ricin, 50 ng/mL SEB, 1000 ng/mL VEE, or 10,000 CFU/mL YP) and background signal in the absence of analyte. The table shows that the dry and wet assays perform comparably.

| | Signal on Specific Spot | | | |
|---|---|---|---|---|
| | Dry | | Wet | |
| Analyte | Backrd | Signal | Backrd | Signal |
| BotA | 249 | 12098 | 156 | 4809 |
| Ricin | 81 | 15502 | 94 | 12531 |
| SEB | 75 | 9518 | 68 | 6299 |
| VEE | 212 | 11821 | 260 | 7497 |
| YP | 115 | 4280 | 145 | 3876 |

Example 6. Assays in Multi-Well Plates with Assay Wells and Desiccant Wells

This assay used a MULTI-SPOT plate configured as shown in FIG. 9. The plate was similar to that shown in FIG. 8 except for the inclusion of conduits 910 connecting pairs of adjacent wells. The conduits were provided by shallow notches that were cut into the walls separating adjacent wells. In this example, one well of each pair of wells was used to carry out a multiplexed immunoassay and the other was used to hold desiccant for maintaining the assay well in a dry state during storage. The assay used a multiplexed sandwich immunoassay with dry capture and detection reagents prepared as in Example 5. The capture antibodies were anti-*Bacillus subtilis* var. *Niger* (BG), anti-MS2 phage, anti-FL, anti-DNP, and mouse IgG as a negative control. The dry detection antibody pill included labeled anti-BG, anti-MS2, and anti-ovalbumin (Ova) (for detecting FL-Ova and DNP-Ova).

After the plates were prepared, the desiccant wells were filled with roughly 50 nag to 200 mg of silica gel or DRIERITE (calcium sulfate) desiccants and the plates were sealed with an aluminum foil heat seal. After sealing the foil seal to the plate top, the notches in the wells provided conduits between the sets of assay and desiccant wells. Some plates were prepared with no desiccant in the desiccant wells for comparison. The plates were kept at 4° C. under dry conditions for several days to allow the dry reagents to fully dry. The plates were then exposed to elevated temperature and humidity for several days prior to using them to carry out measurements of the target organisms (using the assay protocol of Example 5).

FIG. 10 provides signals for samples containing defined amounts of the target analytes and compares the signals from plates with silica desiccant, calcium sulfate desiccant and no desiccant after exposure to 60% humidity at 30° C. for 7 days. Signals are provided as a percentage of the signal obtained from a plate that was prepared at the same time as the others but that had been kept dry a 4° C. for the 7 day period. The results indicate that the desiccant wells were very effective at improving the stability of the dry reagents to heat and humidity.

Patents, patent applications, and publications cited in this disclosure are incorporated by reference in their entirety.

The present invention is not to be limited in scope by the specific embodiments described herein. Indeed, various modifications of the invention in addition to those described herein will become apparent to those skilled in the art from the foregoing description and accompanying drawings. Such modifications are intended to fall within the scope of the claims.

A claim which recites "comprising" allows the inclusion of other elements to be within the scope of the claim; the invention is also described by such claims reciting the transitional phrases "consisting essentially of" (i.e., allowing the inclusion of other elements to be within the scope of the claim if they do not materially affect operation of the invention) or "consisting of" (i.e., allowing only the elements listed in the claim other than impurities or inconsequential activities which are ordinarily associated with the invention) instead of the "comprising" term. Any of these three transitions can be used to claim the invention.

We claim:

1. A multi-well assay plate comprising a plate body with a plurality of wells defined therein comprising:
   (a) a plurality of detection wells, wherein each detection well comprises a binding surface having a capture reagent immobilized thereon and
   (b) a plurality of reagent reconstitution wells, wherein each reagent reconstitution well comprises a reconstitutable labeled detection reagent,
   wherein at least one detection well and one reagent reconstitution well comprises matched capture and detection reagents for measuring an analyte of interest, and wherein said capture reagent and said reconstitutable labeled detection reagent are not in the same well.

2. A multi-well assay plate comprising a plate body with a plurality of wells defined therein comprising:
   (a) a plurality of detection wells, wherein said detection wells
      (i) having well floors and well walls, wherein said well walls have inner wall surfaces and outer wall surfaces,
      (ii) are arranged in a regular two dimensional pattern, and
      (iii) comprise, on an inner surface of each of said detection wells, a binding surface having capture reagent immobilized thereon an array; and
   (b) a plurality of reagent reconstitution wells, wherein said reagent reconstitution wells
      (i) have well floors and well walls, wherein said well walls are defined by outer wall surfaces of said detection wells and by rib elements connecting the outer wall surface of adjacent detection wells and
      (ii) comprise, in each reagent reconstitution well, a reconstitutable dry labeled detection reagent;
   wherein at least one detection well and one reagent reconstitution well comprise matched capture and detection reagents for measuring an analyte of interest, and wherein said capture reagent and said reconstitutable dry labeled detection reagent are not in the same well.

3. The multi-well assay plate of claim 2, wherein said detection wells have well opening perimeters with no reentrant angles or curves and said reagent reconstitution wells have well opening perimeters with reentrant curves or angles.

4. The multi-well assay plate of claim 2, wherein said detection wells have well opening perimeters that are round.

5. The multi-well assay plate of any one of claims 2, wherein said detection and reagent reconstitution wells can be grouped into a plurality of assay sets consisting of one or more detection wells and one reagent reconstitution well, and said detection well(s) and reagent reconstitution well within a set comprise matched capture and detection reagents for measuring an analyte of interest.

6. The multi-well assay plate of claim 5, wherein said sets consist of one detection well and one reagent reconstitution well.

7. The multi-well assay plate of any one of claims 2, wherein said detection well(s) or said reagent reconstitution well further comprises a reconstitutable dry assay control analyte.

8. The multi-well assay plate of any one of claims 2 further comprising one or more additional immobilized capture reagents, wherein said capture reagent and additional capture reagents form a patterned array of binding domains on said binding surface, and said binding domains differ in specificity or affinity for binding partners.

9. The multi-well assay plate of claim 8, wherein said reconstitutable dry reagent further comprises one or more additional labeled detection reagents, and said detection reagent and additional detection reagents differ in specificity or affinity for binding partners.

10. The multi-well assay plate of claim 2, wherein said binding surface is an electrode for use in an electrochemiluminescence assay.

11. A multi-well plate comprising a plate body with a plurality of wells defined therein comprising:
    (a) a plurality of first reagent wells holding a reconstitutable first dry reagent and
    (b) a plurality of second reagent wells holding a second dry reagent,
    wherein said first and second reagents are matched reagents for conducting an assay, and wherein said reconstitutable first dry reagent and second dry reagent are not in the same well.

12. The multi-well assay plate of claim 11, wherein
    said first reagent wells are arranged in a regular two dimensional pattern and said first reagent wells have well floors and well walls, said well walls having inner wall surfaces and outer wall surfaces and
    said second reagent wells have well floors and well walls, said well walls being defined by outer wall surfaces of said detection wells and by rib elements connecting the outer wall surfaces of adjacent detection wells.

13. The multi-well assay plate of claim 12, wherein said detection wells are arranged in an 8×12 array.

14. The multi-well assay plate of claim 12, wherein said first reagent wells have well opening perimeters that are round.

* * * * *